(12) United States Patent
Covalin

(10) Patent No.: US 10,695,568 B1
(45) Date of Patent: Jun. 30, 2020

(54) DEVICE AND METHOD FOR THE TREATMENT OF SUBSTANCE USE DISORDERS

(71) Applicant: Spark Biomedical, Inc, Friendswood, TX (US)

(72) Inventor: Alejandro Covalin, Los Angeles, CA (US)

(73) Assignee: Spark Biomedical, Inc., Friendswood, TX (US)

( * ) Notice: Subject to any disclaimer, the term of this patent is extended or adjusted under 35 U.S.C. 154(b) by 0 days.

(21) Appl. No.: 16/510,930

(22) Filed: Jul. 14, 2019

Related U.S. Application Data

(60) Provisional application No. 62/777,569, filed on Dec. 10, 2018.

(51) Int. Cl.
*A61N 1/36* (2006.01)
*A61N 1/04* (2006.01)
*A61H 39/00* (2006.01)
*A61K 31/485* (2006.01)

(52) U.S. Cl.
CPC ....... *A61N 1/36089* (2013.01); *A61H 39/002* (2013.01); *A61N 1/0456* (2013.01); *A61H 2205/027* (2013.01); *A61K 31/485* (2013.01); *A61N 1/36021* (2013.01); *A61N 1/36053* (2013.01)

(58) Field of Classification Search
CPC ............ A61N 1/36036; A61N 1/36053; A61N 1/0526
See application file for complete search history.

(56) References Cited

U.S. PATENT DOCUMENTS

| 4,014,323 | A | 3/1977 | Gilmer et al. |
| 4,690,144 | A | 9/1987 | Rise et al. |
| 4,865,048 | A | 9/1989 | Eckerson |
| 4,966,164 | A | 10/1990 | Colsen et al. |

(Continued)

OTHER PUBLICATIONS

Filppelli, et al., Non-insertive Acupuncture and Neonatal Abstinence Syndrome: A Case Series From an Inner-city Safety Net Hospital, Global Advances in Health and Medicine, vol. 1, No. 4, Sep. 2012, pp. 48-52.

(Continued)

*Primary Examiner* — George R Evanisko
(74) *Attorney, Agent, or Firm* — Gardella Grace P.A.

(57) ABSTRACT

A treatment system and method for inducing endogenous release of peptides is provided including a concha apparatus including a first electrode in contact with vagal related neural structures; an earpiece connected to the concha apparatus by a first connector, the earpiece including a PCB layer including a second electrode configured to be in contact with a neural structure related to the auriculotemporal nerve, and at least another electrode configured to be in contact with or in proximity to neural structures related to the great auricular nerve and/or its branches and/or the lesser occipital nerve and/or its branches, and an adhesive configured to secure the electrodes on the earpiece to the skin; and a pulse generator connected to the earpiece by a second connector, the pulse generator including circuitry in communication with the first electrode of the concha apparatus, the second electrode and the at least another electrode of the earpiece.

20 Claims, 20 Drawing Sheets

(56) References Cited

U.S. PATENT DOCUMENTS

| | | | |
|---|---|---|---|
| 5,514,175 A * | 5/1996 | Kim | A61H 39/002 607/115 |
| 5,593,432 A | 1/1997 | Crowther et al. | |
| 6,567,702 B1 | 5/2003 | Nekhendzy et al. | |
| 6,697,670 B2 | 2/2004 | Chomenky et al. | |
| 7,797,042 B2 | 9/2010 | Dietrich et al. | |
| 7,856,275 B1 * | 12/2010 | Paul | A61N 1/0496 607/55 |
| 7,986,996 B2 | 7/2011 | Bell | |
| 8,506,469 B2 | 8/2013 | Dietrich et al. | |
| 8,666,502 B2 | 3/2014 | Hartlep et al. | |
| 8,688,239 B2 | 4/2014 | Hartlep et al. | |
| 8,700,163 B2 | 4/2014 | Terry, Jr. et al. | |
| 8,751,020 B2 | 6/2014 | Beck et al. | |
| 8,885,861 B2 | 11/2014 | Beck et al. | |
| 8,942,814 B2 | 1/2015 | Szeles | |
| 8,965,518 B2 | 2/2015 | Ellrich et al. | |
| 9,089,691 B2 | 7/2015 | Libbus et al. | |
| 9,216,290 B2 | 12/2015 | Terry, Jr. et al. | |
| 9,314,611 B2 | 4/2016 | Zschaeck et al. | |
| 9,662,269 B2 * | 5/2017 | Brown | A61H 39/002 |
| 9,839,577 B2 | 12/2017 | Brown et al. | |
| 10,010,479 B2 | 7/2018 | Brown et al. | |
| 10,058,478 B2 | 8/2018 | Schnetz et al. | |
| 2005/0165460 A1 | 7/2005 | Erfan | |
| 2006/0064139 A1 * | 3/2006 | Chung | A61M 21/00 607/45 |
| 2007/0250145 A1 | 10/2007 | Kraus et al. | |
| 2008/0021517 A1 | 1/2008 | Dietrich | |
| 2008/0021520 A1 | 1/2008 | Dietrich | |
| 2008/0051852 A1 | 2/2008 | Dietrich et al. | |
| 2008/0249594 A1 | 10/2008 | Dietrich et al. | |
| 2009/0287035 A1 | 11/2009 | Dietrich et al. | |
| 2010/0057154 A1 | 3/2010 | Dietrich et al. | |
| 2010/0262205 A1 | 10/2010 | De Ridder | |
| 2011/0166624 A1 | 7/2011 | Dietrich et al. | |
| 2013/0079862 A1 | 3/2013 | Ellrich | |
| 2013/0150923 A1 | 6/2013 | Schnetz et al. | |
| 2013/0231729 A1 | 9/2013 | Hartlep et al. | |
| 2013/0231730 A1 | 9/2013 | Hartlep et al. | |
| 2014/0046406 A1 | 2/2014 | Ellrich et al. | |
| 2014/0126752 A1 | 5/2014 | Beck et al. | |
| 2014/0135886 A1 | 5/2014 | Cook et al. | |
| 2015/0018926 A1 * | 1/2015 | Frenkel | A61N 1/36036 607/139 |
| 2015/0080986 A9 | 3/2015 | Ellrich et al. | |
| 2017/0296807 A1 | 10/2017 | Brown et al. | |
| 2017/0368329 A1 | 12/2017 | Tyler et al. | |
| 2018/0200522 A1 | 7/2018 | Taca, Jr. | |
| 2018/0296435 A1 | 10/2018 | Brown et al. | |

OTHER PUBLICATIONS

Raith, et al., Laser Acupuncture as An Adjuvant Therapy for a Neonate with Neonatal Abstinence Syndrome (Nas) Due to Maternal Substitution Therapy: Additional Value of Acupuncture, Acupuncture in Medicine, vol. 32, Issue 6, Dec. 1, 2014, pp. 523-524.
Han, et al., Mobilization of Specific Neuropeptides by Peripheral Stimulation of Identified Frequencies, Physiology, vol. 7, Issue 4, Aug. 1, 1992, pp. 176-180.
Han, Ji-Sheng, Acupuncture and Endorphins, Neuroscience Letters, No. 361, 2004, pp. 258-261.
Meade, et al., A Randomized Trial of Transcutaneous Electric Acupoint Stimulation As Adjunctive Treatment for Opioid Detoxification, Journal of Substance Abuse Treatment, vol. 38, Issue 1, Jan. 2010, pp. 12-21.

* cited by examiner

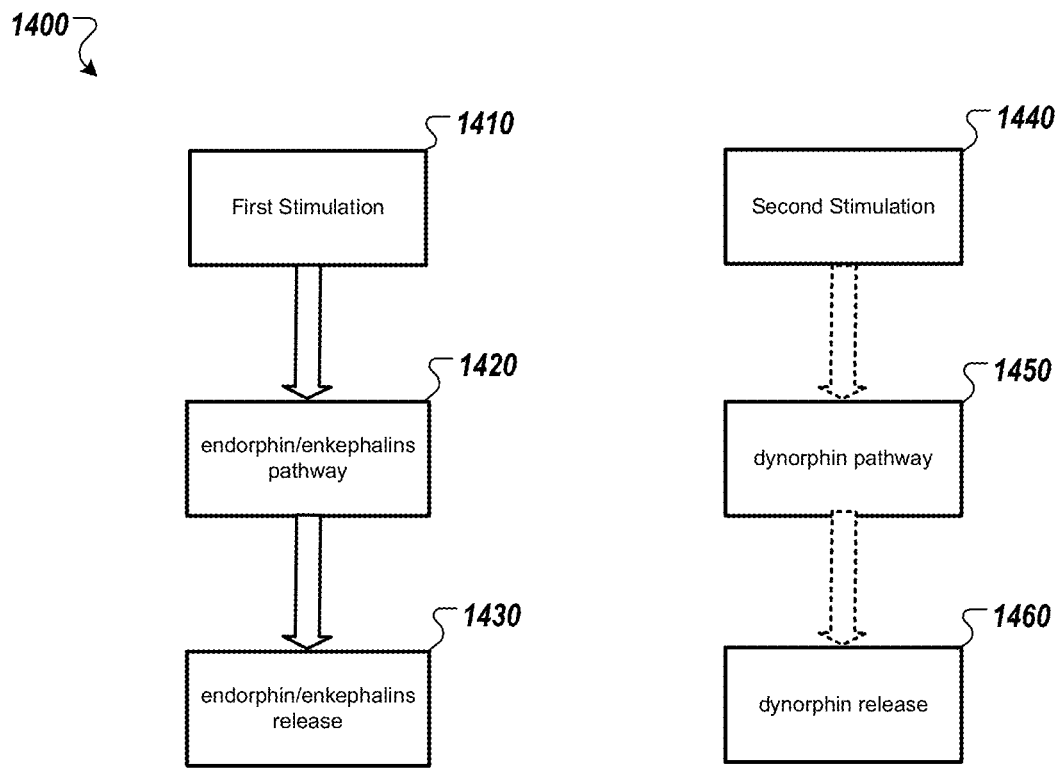
FIG. 14A
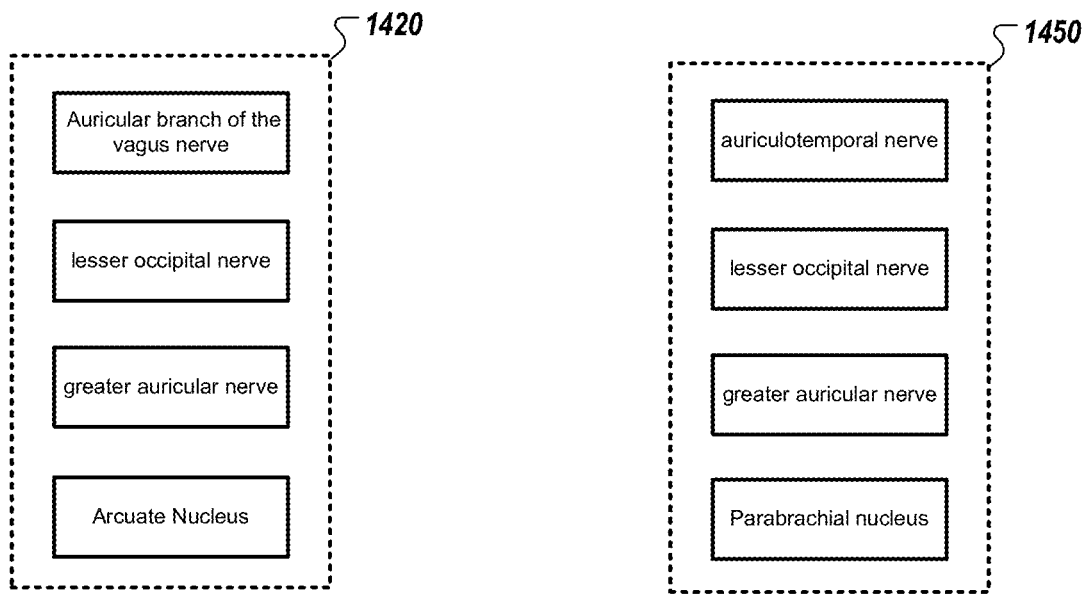
FIG. 14B
FIG. 14C

DEVICE AND METHOD FOR THE TREATMENT OF SUBSTANCE USE DISORDERS

RELATED APPLICATIONS

This application claims priority to U.S. Provisional Patent Application Ser. No. 62/777,569, entitled "Device and Method for the Treatment of Substance Use Disorders," filed Dec. 10, 2018. All above identified applications are hereby incorporated by reference in their entireties.

BACKGROUND

According to the National Survey on Drug Use and Health, approximately 2.1 million Americans are addicted to opioid pain relivers (OPRs), and 513,000 are addicted to heroin. In 2017 there are a record 72,000 overdose deaths, a rise of approximately 10% nationwide; largely fueled by new, synthetic opioids. The National Institutes of Health (NIH) reported that in the United States alone there are more than 115 deaths every day related to opioids. Opioids produce a strong physiological dependence on its users; it is this dependence that makes it extremely difficult, if not impossible, for user willing to stop consuming this type of drug to do so without the intervention of a healthcare professional.

The physiological reaction caused by stopping opioid intake is known as Opioid Withdrawal. Opioid Withdrawal is generally extremely unpleasant and in some unattended cases may lead to death. The over usage of opioids in the country has reach such levels that the government has labeled the current situation as a national crisis. Interventions are needed to help alleviate the Opioid Withdrawal symptoms felt by individuals who are in the process of stopping opioid consumption.

Addressing strategies for addiction treatment and recovery has become a major priority for government agencies given the substantial impact on health, social, and economic welfare. Treatment of opioid addiction includes pharmacotherapies and psychosocial and behavioral adaptation approaches including: residential treatment, mutual-help, and 12-Step treatment programs. In many cases these interventions may be administered alone or in combination with pharmacotherapy. Psychosocial opioid addiction treatment approaches show value and are an important treatment option. However, treatments with greater specificity, consistency, and patient compliance is needed.

SUMMARY OF ILLUSTRATIVE EMBODIMENTS

The forgoing general description of the illustrative implementations and the following detailed description thereof are merely exemplary aspects of the teachings of this disclosure, and are not restrictive.

In an exemplary embodiment, a wearable treatment system for providing transcutaneous stimulation for inducing endogenous release of peptides, includes a concha apparatus including a first electrode configured to be in contact with vagal related neural structures; an earpiece connected to the concha apparatus by a first connector, the earpiece including an insulated electronics layer including a second electrode configured to be in contact with a neural structure related to the auriculotemporal nerve, and at least another electrode configured to be in contact with or in proximity to neural structures related to at least one of the great auricular nerve and/or its branches and/or the lesser occipital nerve and/or its branches, and an adhesive configured to secure at least one of the earpiece and the electrodes on the earpiece to the skin surrounding an ear of a patient; and a pulse generator configured to be connected to the earpiece by a second connector, the pulse generator including circuitry in communication with the first electrode of the concha apparatus, the second electrode and the at least another electrode of the earpiece.

In some implementations, the treatment system includes a peripheral device configured to be in communication with the pulse generator and configured to modify a stimulation parameter provided to at least one electrode.

In some implementations, the pulse generator includes a low power field-programmable gate array for controlling therapy delivery.

In some implementations, the stimulation parameter is configured to provide synchronized stimulations between the concha apparatus and the earpiece configured to balance a ratio of activity between at least one of the autonomic nervous system and the parasympathetic nervous system, the autonomic nervous system and the sympathetic nervous system, and the parasympathetic nervous system and the sympathetic nervous system.

In some implementations, at least one of the second electrode and the at least another electrode is comprised of a grouping of two or more electrodes.

In some implementations, the treatment system includes a multiplexor in communication with two or more of the electrodes on the earpiece and configured to direct stimulation pulses towards at least one of the two or more of the electrodes on the earpiece.

In some implementations, the treatment system includes a conductive adhesive coating on each electrode.

In some implementations, the treatment system includes at least one actuator disposed between electrodes on the earpiece.

In some implementations, the concha apparatus has a first member on its distal end configured to fit within natural extrusions and notches of the ear and a second member on its proximal end configured to fit within natural extrusions and notches of the ear.

In some implementations, the concha apparatus includes a spring configured to stress a structure of the concha apparatus to facilitate placement of the first electrode.

In some implementations, the structure of the concha apparatus is configured to be mechanically stressed to facilitate secure placement of the first electrode to the skin.

In some implementations, the treatment system is configured to provide endogenous release for treating substance use disorder and pain.

In some implementations, the treatment system is configured to provide therapy for treatment of neonatal abstinence syndrome.

In some implementations, the treatment system is configured to induce neuronal plasticity for at least one of provoking cognitive improvements, stroke recovery, PTSD, phobias, ADHD, ADD, dementia including treating Alzheimer's disease.

In some implementations, the treatment system is configured to be used to restore autonomic imbalance including at least one of cardiac heart failure, atrial fibrillation, anxiety, stress, gastric motility, depression, cluster headaches, and migraines.

In an exemplary embodiment, a wearable treatment device for providing transcutaneous stimulation for inducing endogenous release of peptides, includes a concha apparatus including a first electrode configured to be in contact with vagal related neural structures; and an earpiece connected to the concha apparatus by a connector, the earpiece including an insulated electronics layer including a second electrode configured to be in contact with a neural structure related to the auriculotemporal nerve, and at least another electrode configured to be in contact with or in proximity to neural structures related to at least one of the great auricular nerve and/or its branches and/or the lesser occipital nerve and/or its branches, and an adhesive configured to secure the electrodes on the earpiece to the skin; and wherein the treatment device is configured to be connected to a pulse generator, the pulse generator including circuitry configured to be in communication with the first electrode of the concha apparatus, and the second electrode and the at least another electrode of the earpiece.

In an exemplary embodiment, a method for inducing endogenous release of peptides, including adhering a therapy device to an outer portion of a patient's skin including a concha apparatus including a first electrode configured to be in contact with vagal related neural structures, an earpiece connected to the concha apparatus by a first connector, the earpiece including an insulated electronics layer including a second electrode configured to be in contact with a neural structure related to the auriculotemporal nerve, and at least another electrode configured to be in contact with or in proximity to neural structures related to at least one of the great auricular nerve and/or its branches and/or the lesser occipital nerve and/or its branches; connecting the therapy device to a pulse generator including circuitry configured to be in communication with the first electrode of the concha apparatus, and the second electrode and the at least another electrode of the earpiece; providing a first stimulation to the first electrode at a first tissue location configured to stimulate a first pathway for modulating a first release of a first endogenous peptide; and providing a second stimulation at a second tissue location configured to stimulate a second pathway for modulating a second release of a second endogenous peptide.

In some implementations, the first stimulation is a high frequency stimulation and the second stimulation is a low frequency stimulation.

In some implementations, the first stimulation is configured to stimulate a dynorphin pathway including at least one of the auriculotemporal nerve, the lesser occipital nerve, and the great auricular nerve.

In some implementations, the second stimulation is configured to stimulate at least one of an endorphin pathway and enkephalin pathway including at least one of the auricular branch of the vagus nerve, the lesser occipital nerve, the great auricular nerve, and the arcuate nucleus.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIG. 14A is a flow chart of a method for providing therapy including providing a first stimulation at a first tissue location configured to stimulate a first pathway for modulating a first release of a first endogenous peptide and a second stimulation at a second tissue location configured to stimulate a second pathway for modulating a second release of a second endogenous peptide according to an example;

FIG. 14B are examples of target locations for stimulation of the first tissue location;

FIG. 14C are examples of target locations for stimulation of the second tissue location;

DETAILED DESCRIPTION OF ILLUSTRATIVE EMBODIMENTS

Figure 1A:
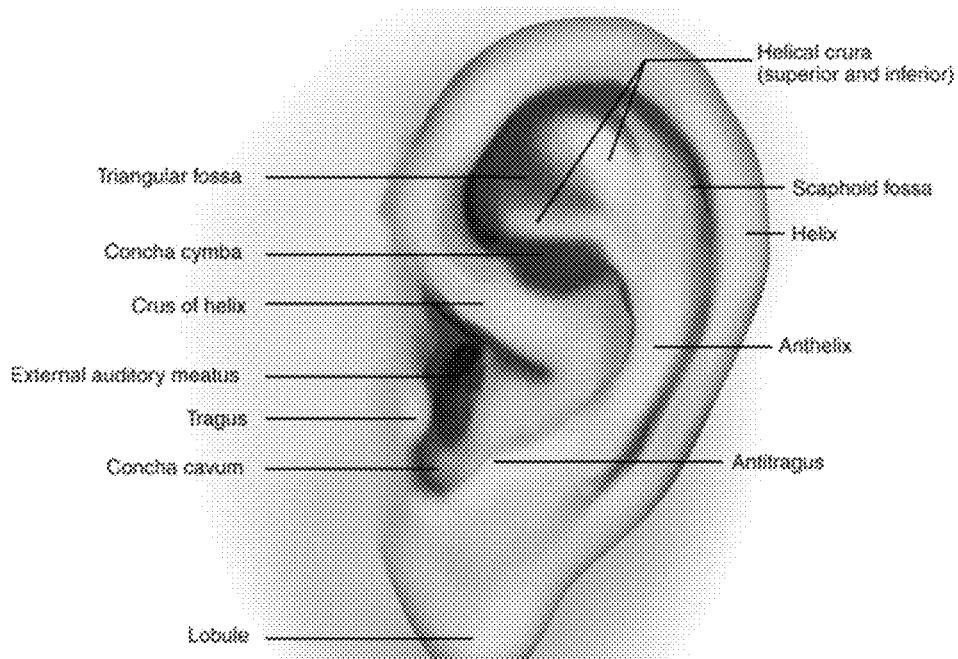
FIG. 1A is a drawing identifying structures of an ear according to an example.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

Currently, the United States is experiencing an opioid epidemic in the use of prescription and non-prescription drugs that has continued to rise since the 1990's. The need for safe and effective opioid withdrawal treatment is demanding and largely unmet. According to the National Survey on Drug Use and Health (NSDUH), approximately 2.1 million Americans are addicted to opioid pain relivers (OPRs), and 513,000 are addicted to heroin. In 2005, there were an estimated 10 million chronic pain patients receiving daily, long-term treatment with OPRs. The continuing increase in opioid consumption from 2005 to 2017 suggests that the number may now exceed 11 million.

A primary constraint on the overall percentage of treatment recipients is the limited availability of licensed physicians that can prescribe pharmacotherapies. Additionally, prescription opioids pose a variable level of risk on respiratory depression and abnormal cardiac activity, thus can only be obtained from licensed opioid treatment programs (OTPs). The lack of OTPs in many communities presents a major challenge to expanding access to methadone. In contrast, buprenorphine, a partial opioid agonist, has demonstrated a better safety profile compared to methadone and can be prescribed in an office-based setting. However, buprenorphine includes federal limits on the number of patients a physician may treat, ineligibility of nurse practitioners to prescribe it, and inadequate integration of buprenorphine into primary care treatment.

Pharmacotherapies for opioid withdrawal include full-agonist treatment with methadone, partial-agonist with buprenorphine, and full-antagonist with naltrexone. Methadone and buprenorphine are semi-synthetic opioid derivatives that bind to opioid receptors and allow addicted individuals to discontinue the misuse of opioids without experiencing withdrawal symptoms. Buprenorphine can produce typical opioid effects and side effects such as euphoria and respiratory depression, however, its maximal effects are less than those of full agonists like methadone or heroin. Dose response curves specific to the agonist effects of buprenorphine increase linearly with higher doses of the drug until it reaches a plateau.

Buprenorphine can block the effects of full opioid agonists (i.e. methadone and heroin) and can precipitate withdrawal symptoms if administered to an opioid-addicted individual while a full agonist is in the bloodstream. Buprenorphine has a higher affinity than other opioids and as such will compete for the receptor and occupy that receptor blocking other opioids from binding. If there is an insufficient amount of buprenorphine to occupy and satisfy the receptors, withdrawal symptoms can occur; in which case additional buprenorphine is given until withdrawal symptoms disappear.

Lastly, naltrexone is an opioid-antagonist that competes for opioid-receptors and displaces opioid drugs from these receptors, thus reversing the effects of opioids. Naltrexone is capable of antagonizing all opioid receptors, but has a higher affinity to μ- rather than κ- and δ-receptors. By blocking the μ-opioid receptor, naltrexone acts to decrease the dopamine reward. The activity of naltrexone is thought to be a result of both the parent and its 6β-naltrexol metabolite. Naltrexone's mechanism of action is similar to naloxone (opioid antagonist; found in Suboxone) except that it is longer acting. Naltrexone can be administered with a long-acting injection formulated in microspheres that persists for 1 month after a single injection.

Due to inadequate and scarce treatment options, finding an effective non-pharmacological approach would be critical in improving and expanding treatment for opioid withdrawal and addiction. Abundant clinical evidence exists for the rapid and effective reduction of signs and symptoms associated with opioid withdrawal through various approaches of non-invasive neurostimulation.

Anecdotal evidence exists for the rapid and effective attenuation of signs and symptoms associated with opioid withdrawal through neurostimulation.

Figure 1B:
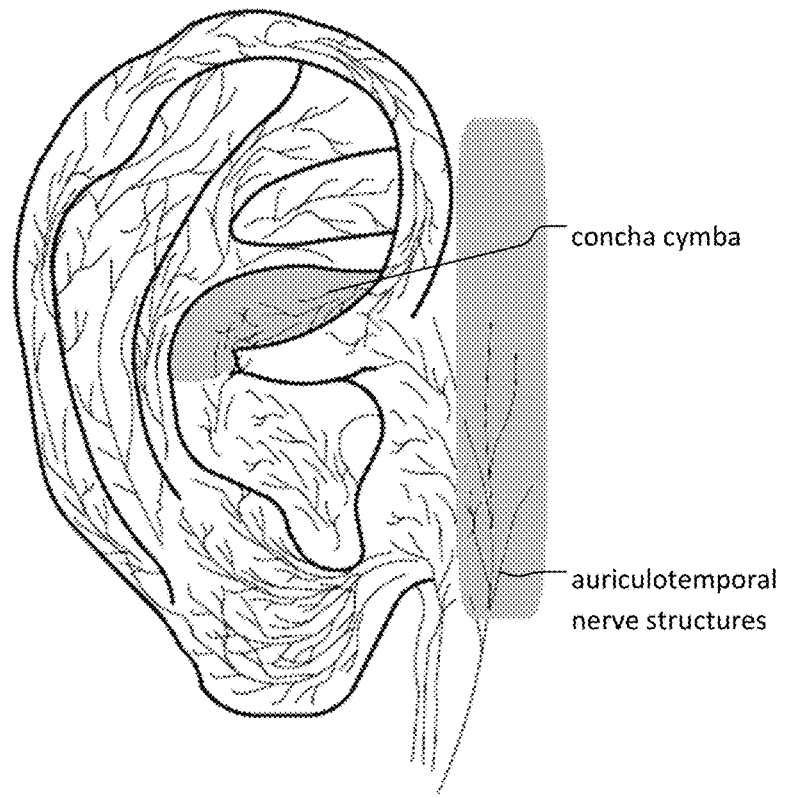
FIG. 1B is a drawing of innervations of the ear amongst which are vagal related neural structures, auriculotemporal nerve structures, neural structures related to the lesser occipital nerve, and neural structures related to the great auricular nerve.

FIG. 1A is a drawing identifying structures of an ear showing amongst other the concha cymba, the tragus, the antihelix, the helix, the external auditory meatus, and the Lobule. FIG. 1B is a drawing of innervations of the ear amongst which are vagal related neural structures, for example within the concha cymba, auriculotemporal nerve structures, for example rostral to the auricle, neural structures related to the lesser occipital nerve, for example along the antihelix, and neural structures related to the great auricular nerve, for example on the lobule region.

Figure 1C:
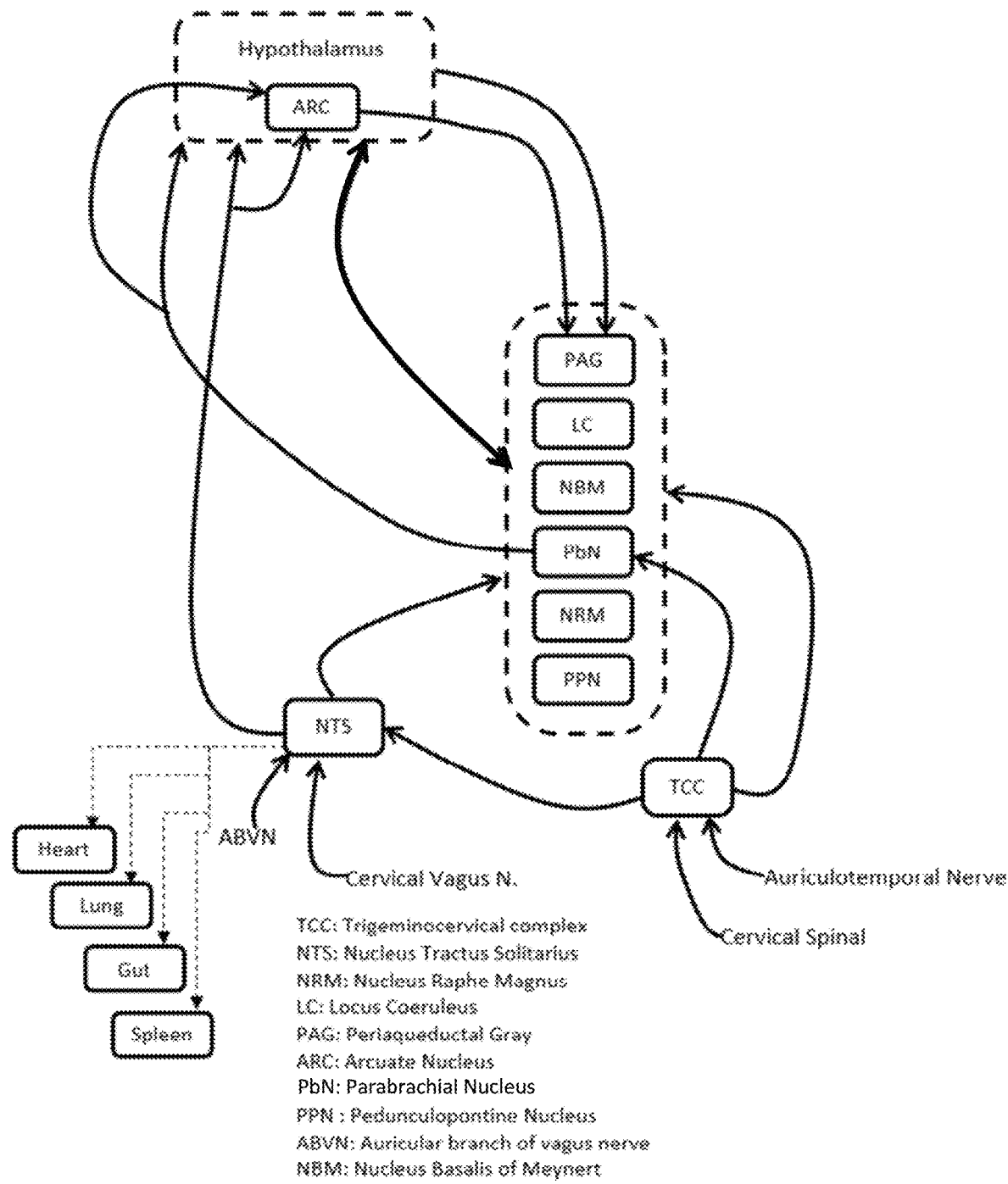
FIGS. 1C-1E are drawings identifying neural structures and pathways for modulating the release of endogenous opiate receptor agonist, which modulate pain, as well as pathways modulating inflammatory and cognitive processes to an example.
Figure 1D:
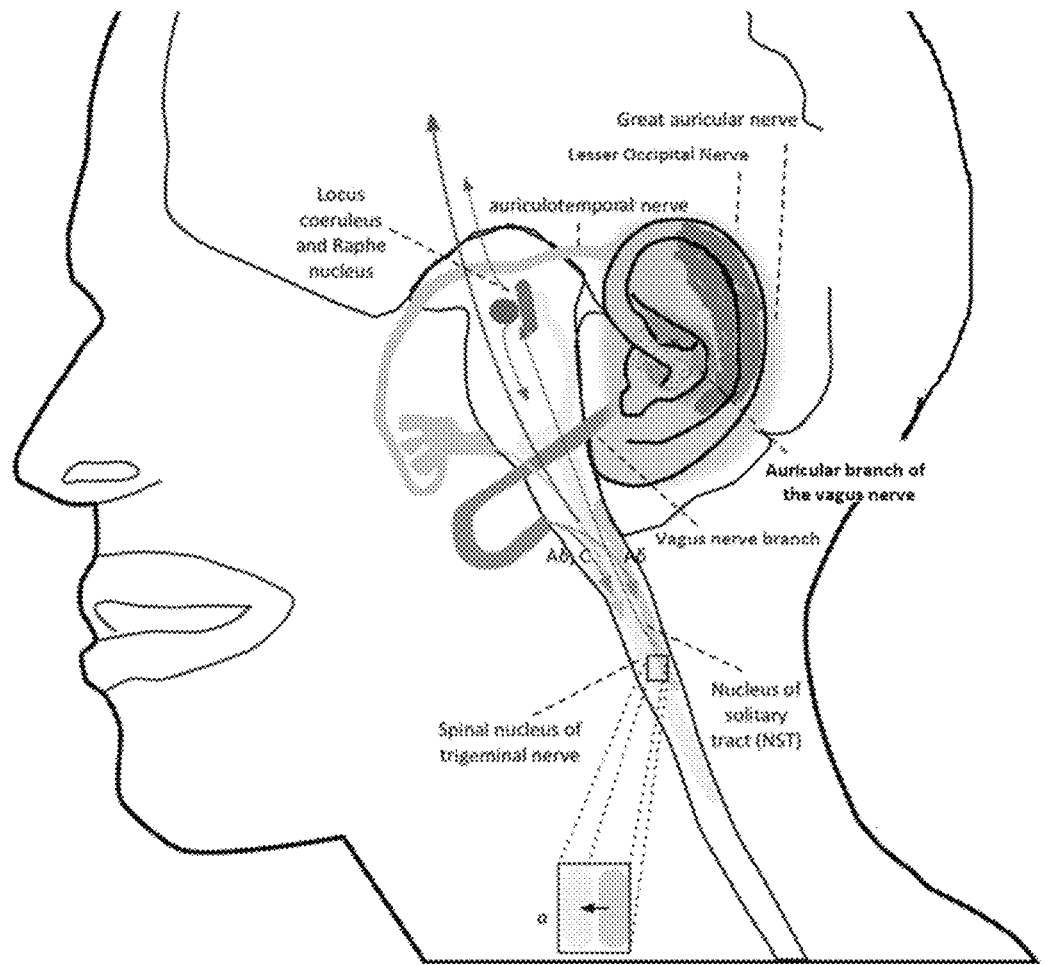
Figure 1E:
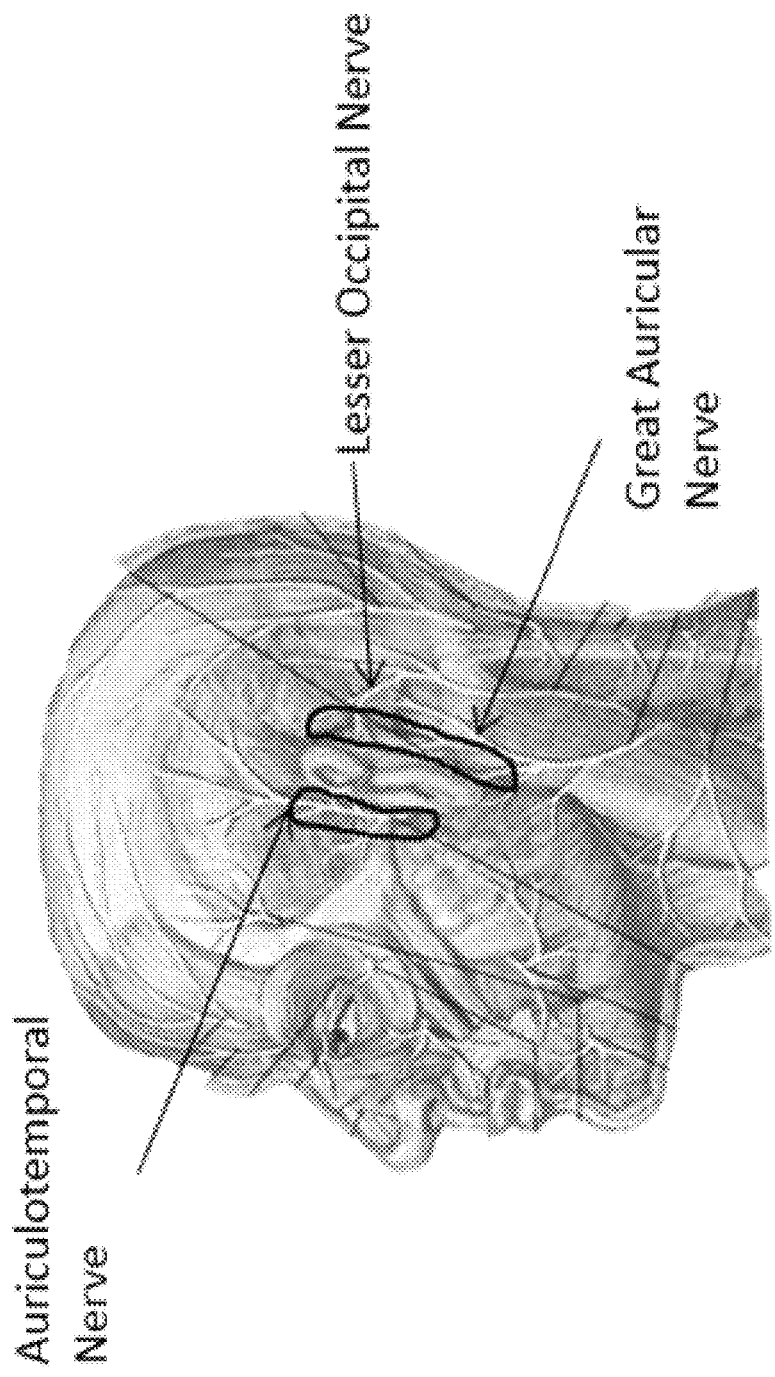

FIGS. 1C-1E are drawings identifying neural structures and pathways for modulating the release of endogenous opioid receptor agonist, which modulate pain, as well as pathways modulating inflammatory and cognitive processes. The Nucleus of the solitary tract (NTS) receives afferent connections from many areas including the Trigemino-cervical complex (TCC), the cervical vagus nerve as well as from the auricular branch of the vagus nerve (ABVN). The TCC is a region in the cervical and brain stem area were trigeminal and occipital fibers synapse, including the Auriculotemporal nerve, the lesser occipital nerve and the greater auricular nerve. The TCC projects to multiple areas in the brain stem including, but not limited to the Nucleus Raphe Magnus (NRM), the Locus Coeruleus (LC), Periaqueductal Gray (PAG), Nucleus Basalis (NBM) and Parabrachial nucleus (PbN). The NTS also among others, also projects to the Nucleus Raphe Magnus, the Locus Coeruleus, and the Periaqueductal Gray as well as to high centers like the hypothalamus, including into the Arcuate Nucleus (ARC) which receives its majority of non-intrahypothalamic afferents from the NTS. Additionally, many interconnections exist amongst different brainstem nuclei (e.g., PAG, LC, NRM, NBM, PbN, PPN).

These connections make this neural circuit extremely important for modulating pain, as production of endorphins, enkephalins, and dynorphins are modulated by this circuit. In addition, this neural circuits are crucial for learning and memory as well as for arousal and wakefulness. For example, an interaction between norepinephrine, produced by activity in the Locus Coeruleus, Serotonin (5-HT), produced by activity in the Nucleus Raphe Magnus, and Acetylcholine (Ach) produced by activity in the Pedunculopontine Nucleus (PPN) or NBM is extremely important for memory and learning. Arousal and wakefulness is modulated, amongst others, by norepinephrine in the brain.

There are descending indirect connections going to the heart, Lungs, Gut, and spleen. Indirect connections include connections where there is at least one synapse elsewhere before reaching the target. This means that modulating the activity of these neural circuits can affect the respective organs. In particular, heart rate can be modulated, for example, heart rate can be decreased and heart rate variability can be increased; oxygen absorption can be increased at the lungs by increasing the compliance of the bronchi tissue and thus increasing the oxygen transport availability therefore increasing the potential for more oxygen to be absorbed into the blood; gut motility can be increased by descending pathways originating in the dorsal motor nucleus of the vagus nerve (DMV); since DMV activity is modulated by NTS activity, motility in the gut can be affected by modulating the activity in the NTS; and a decrease in circulating pro-inflammatory cytokines can be achieved by modulating spleen activity via NTS descending pathways.

There are at least three different opioid receptors, Mu (μ), Delta (δ), and Kappa (κ) in pain modulation. The body produces endogenous agonist peptides for each of these three receptors. These peptides are called endorphins, which primarily binds to the Mu (μ) receptors, Enkephalin which primarily binds to the Delta (δ) receptors, and Dynorphins, which primarily binds to the Kappa (κ) receptors. Pain studies suggest that production of these endogenous peptides follow different pathways. While production of endorphins and enkephalin is mediated by activity in the Arcuate Nucleus (ARC) in the hypothalamus, activity in the Parabrachial nucleus mediates production of dyanophins. Furthermore, electrostimulation experiment showed that dynorphin production was more efficiently mediated by higher frequency than production of the endorphins and/or enkephalins; this suggests that while the dynorphin pathway is more efficiently activated by higher frequencies, the endorphins and enkephalins pathway is more efficiently activated by lower frequencies.

Percutaneous neurostimulation requires a percutaneous device which uses small needles implanted into the skin to deliver neurostimulation. Percutaneous neurostimulation systems present numerous disadvantages and limitations, which include: the location of the needles is critical and thus needle insertion must be performed by a trained professional heath provider; the needles must be sterile; needle sterility requirements equate to a minimal device shelf-life; movement or dislodged needles requires the attention of a trained clinic staff member; many patients have inherent fear of needles; currently available systems cannot be re-used, re-charged, or used beyond its immediate battery life; currently available systems do not allow for fully customizable stimulation settings; currently available systems are not capable of determining and reporting if stimulation is being delivered; currently available systems are not capable of gathering device compliance data; and currently available systems are not designed to be easy to use, aesthetically and cosmetically appealing which has an effect on patient compliance.

In an aspect, the system relates to transcutaneous stimulation of auricular nerve fibers for the reduction of substance consumption, the reduction of symptoms associated with substance withdrawal, and for the long-term maintenance to prevent substance relapse. The proposed novel neuromodulation treatment does not require piercing the dermal layers and the required precision is such that any layman can apply the device and receive therapy. In an aspect, the system is not required to be sterile, is easy to apply, and a user can apply without a clinician. The proposed treatment method along with the treatment device overcomes all of the above mentioned disadvantages. Given the large unmet medical need (i.e., opioid overuse), the fact that the treatment device proposed here has not been offered in the manner here proposed points to the non-obviousness nature of the proposed treatment.

A therapy system and method are provided for rapidly releasing endogenously produced opioid receptor agonists. The therapy system includes a treatment device that allows the proposed therapy to be easily and reliably applied by almost anyone at a relatively low cost. Some advantages over the existing neuromodulation treatment and related devices are: ease of use in both the application of the device, customizing therapeutic settings, and the actual wearing of the device, minimal risk of infection, users have the ability to safely self-administer or restart the treatment without the need to go back to a clinic, significantly extended shelf life, reduced anxiety of patient due to non-invasiveness, long-term use option, customizable therapeutic settings, ability to notify user, caregiver, and clinician if therapy is interrupted or halted, ability to report overall usage to clinical staff or users for analysis, and the user does not have go back to the clinic to extend treatment or to use it at any given time when they feel it is needed present a major advantage over existing neuromodulation therapies, opening the door to a long-term maintenance treatment.

Furthermore, patient compliance is one of the primary obstacles to clinical success, the proposed device has been designed to alert the treating clinic staff when the device is not being used as prescribed, including device malfunction, and electrode misplacement. Since the device and therapy can be used long-term and can be easily applied by the user, the novel therapy/device combination lends itself to be used for consumption reduction, consumption secession, and long-term use avoidance.

In some implementations, the treatment device can be used for treating and/or managing symptoms for other indications. In some implementations, the treatment device can be used to provide therapy for the treatment of neonatal abstinence syndrome by transcutaneous stimulation of auricular nerve fibers. Auricular acupuncture has recently been studied as an adjunctive therapy for neonatal abstinence syndrome in newborns. Non-insertive acupuncture (NIA) using traditional needles as shown in a publication by Filippelli, A. C. et. al. (2012). titled "Non-insertive Acupuncture and Neonatal Abstinence Syndrome: A Case Series From an Inner-city Safety Net Hospital. Global Advances in Health and Medicine," published in Global Advances in Health and Medicine, 48-52. 2012, herein incorporated by reference.

Evidence that the treatment device can be used to provide therapy for the treatment of neonatal abstinence syndrome was provided in a study where a handheld laser was applied to the ear of newborns with neonatal abstinence syndrome resulting in some of the babies becoming more relaxed during their course of treatment, as described in Raith, W., & Urlesberger, B. titled "Laser Acupuncture as An Adjuvant Therapy for a Neonate with Neonatal Abstinence Syndrome (NAS) Due to Maternal Substitution Therapy: Additional Value of Acupuncture," published in Acupuncture in Medicine, 2012, 32(6), 523-524 herein incorporated by reference. While more in-depth studies are needed to evaluate Non-insertive acupuncture as an effective adjunct therapy for neonatal abstinence syndrome in newborns, the early results show promise of tapping into the auricular neural pathways for treating neonatal abstinence syndrome.

In an aspect, the therapy device is configured to provide stimulation therapy to release a different type and quantity of endogenous opioid peptides based on varying stimulation parameters. Three families of endogenous opioid peptides have been characterized in the CNS: enkephalins, endorphins, and dynorphins. Supporting animal data was shown in a study examining effects of different stimulation frequencies on the type and quantity of endogenous opioid peptides released, as described in a publication by Han, J. S., and Wang, Q. titled "Mobilization of specific neuropeptides by peripheral stimulation of identified frequencies," in Physiology 1992, 7(4), 176-180, herein incorporated by reference. Electro-acupuncture (EA) stimulation was delivered at two specific acupoints on the hindlimb. Rats were given stimulation at 2, 15, and 100 Hz. Spinal perfusate was collected before and during stimulation. A clear difference in stimulation frequency and type of opioid peptide release were shown including that 2 Hz was effective at releasing enkephalins and beta-endorphins, and 100 Hz most effectively released dynorphin. No increase in opioid peptides was observed in non-responder rats that failed to show a response to tail-flick during stimulation. Although, 15 Hz was capable of releasing enkephalin and dynorphin opioid peptides, another study shows that alternating stimulation at 2 Hz/100 Hz maximized analgesic effects, the study by Han, J. S. titled "Acupuncture and endorphins," published in Neuroscience letters, 2004, 361(1-3), 258-261 is herein incorporated by reference. The scientific evidence that pain-relief is achieved by delivering neurostimulation to release endogenous opioid peptides and fill vacant opioid receptors, was later a tested hypothesis for reducing the symptoms associated with opioid withdrawal.

In a randomized clinical trial, transcutaneous electrical acupoint stimulation (TEAS) was delivered as an adjuvant to opioid detoxification using buprenorphine-naloxone, the clinical trial as reported by Meade, C. S., et al., titled "A randomized trial of transcutaneous electric acupoint stimulation as adjunctive treatment for opioid detoxification, Journal of Substance Abuse Treatment, 2010, 38(1), 12-21, is herein incorporated by reference. Based on the preclinical evidence described above, TEAS was delivered at alternating low (2 Hz) and high (100 Hz) for 30 minutes each day for 3-4 days. In the active TEAS group, patients were 77% less likely to have used any drugs as compared to 33% in sham treatment at 2-weeks post-discharge. Additionally, active TEAS improved pain perception and overall health.

In some implementations, the treatment device can be used to induce neuronal plasticity or Neuroplasticity for provoking cognitive improvements, stroke recovery, PTSD, phobias, ADHD, ADD, dementia including treating Alzheimer's disease. Neuroplasticity underlies learning; therefore, strategies that enhance neuroplasticity during training have the potential to greatly accelerate learning rates. Earlier studies have successfully demonstrated that invasive or implanted vagus nerve stimulation (VNS) can drive robust, specific neural plasticity. Brief bursts of VNS are paired with training to engage pro-plasticity neuromodulatory circuits and reinforce the specific neural networks that are involved in learning. This precise control of neuroplasticity, coupled with the flexibility to be paired with virtually any training paradigm, establishes VNS as a potential targeted neuroplasticity training paradigm.

The vagus nerve is a cranial nerve that is located adjacent to the carotid artery in the neck. Direct stimulation of the vagus nerve activates the nucleus tractus solitarius, which has projections to nucleus basalis (NB) and locus coeruleus (LC). The NB and LC are deep brain structures that release acetylcholine and norepinephrine, which are pro-plasticity neurotransmitters important for learning and memory. Stimulation of the vagus nerve using a chronically implanted electrode cuff is safely used in humans to treat epilepsy and depression and has shown success in clinical trials for tinnitus and motor impairments after stroke. The auricular branch of the vagus nerve innervates the dermatome region of outer ear, being the region known as the cymba conchae one of the areas innervated by it. Non-invasive stimulation of the left auricular branch of the vagus nerve may drive activity in similar brain regions as invasive vagus nerve stimulation. Recently auricular neurostimulation has proven beneficial in treating a number of human disorders.

In some implementations, the treatment device can be used to restore autonomic imbalance such as cardiac heart failure, atrial fibrillation (AF), anxiety, stress, gastric motility, depression, cluster headaches, and migraines. Transcutaneous electrical stimulation of the tragus, the anterior protuberance of the outer ear, where the auricular branch of the Vagus nerve is located can elicit evoked potentials in the brainstem in human subjects. Based on these observations, it was demonstrated that atrial fibrillation inducibility was suppressed by transcutaneous LL-VNS, which was achieved through stimulation of the auricular branch of the vagus nerve at the tragus in a canine. Noninvasive LL-TS increases AF threshold (mitigates risk of AF), as well as alleviates AF burden in both canines and humans. In healthy subjects, LL-TS can also increase heart rate variability and reduce sympathetic outflow.

In an exemplary embodiment, a therapy system includes a treatment device having an auricular component configured to be in contact with a patient and a pulse generator or controller configured to communicate with the treatment device. In some implementations, a treatment device can be provided as an assembled unit or as several pieces configured for connection prior to use. In an example, the auricular component can be provided in a sealed pouch and a pulse generator can be provided to connect the auricular component to a connector on the pulse generator. In an aspect, the system is configured to have a removable stimulator without the need to remove the auricular component and vice-versa. In an example, the earpiece can be placed around the auricle of the patient before or after connection to the pulse generator.

To apply the earpiece around the auricle of the patient, press against the patient's skin such that exposed skin adhesives and adhesives/hydrogels adhere to the skin. Next, place the concha apparatus in the ear such that a first portion of the concha apparatus sits outside the external ear canal in the cavum. Finally, flex a second or distal portion of the concha apparatus supporting the cymba electrode until it goes into the cymba of the ear. In some implementations, the earpiece includes one or more protective liners on one or more of the skin adhesive, the cymba electrode, and the non-cymba electrodes which are to be removed before use.

In some implementations, the treatment device can be used to provide therapy including a first stimulation configured to stimulate pathways modulating dynorphins release and a second stimulation configured to stimulate pathways modulating endorphins release. In some implementations, the treatment device can be used to provide therapy including a first stimulation configured to stimulate pathways modulating dynorphins release and a second stimulation configured to stimulate pathways modulating enkephalins release. In other implementations, the treatment device can be used to provide therapy including a first stimulation configured to stimulate pathways modulating dynorphins release and a second stimulation configured to stimulate pathways modulating enkephalins and endorphins release.

In an example, the first stimulation can be a high frequency stimulation and the second stimulation can be a low frequency. In an example, the pathways modulating dynorphins release can include at least one of the auriculotemporal nerve, the lesser occipital nerve, and the great auricular nerve. In an example, the pathways modulating dynorphins release can include stimulation of dynorphin pathway via stimulation of the Parabrachial nucleus. In an example, the pathways modulating endorphins and enkephalins release can include at least one of the auricular branch of the vagus nerve, the lesser occipital nerve, and the great auricular nerve. In an example, the pathways modulating endorphins and enkephalins release can include stimulation of endorphins and enkephalins pathway via stimulation of the Arcuate nucleus of the hypothalamus.

To provide the therapy, a provider may adjust therapy parameters as needed and start the therapy using the controls on either the pulse generator or the peripheral device. In some implementations, the therapy includes providing two or more simultaneous and/or synchronized stimulations. In an aspect, the therapy can involve applying a first stimulation having a first set of parameters at a first portion of the patient's skin and applying a second stimulation having a second set of parameters at a second portion of the patient's skin. When therapy is done, the user may remove the earpiece and disconnect the earpiece from the pulse generator. In an example, the used earpiece can be replaced with a new earpiece for the next session.

Figure 2A:
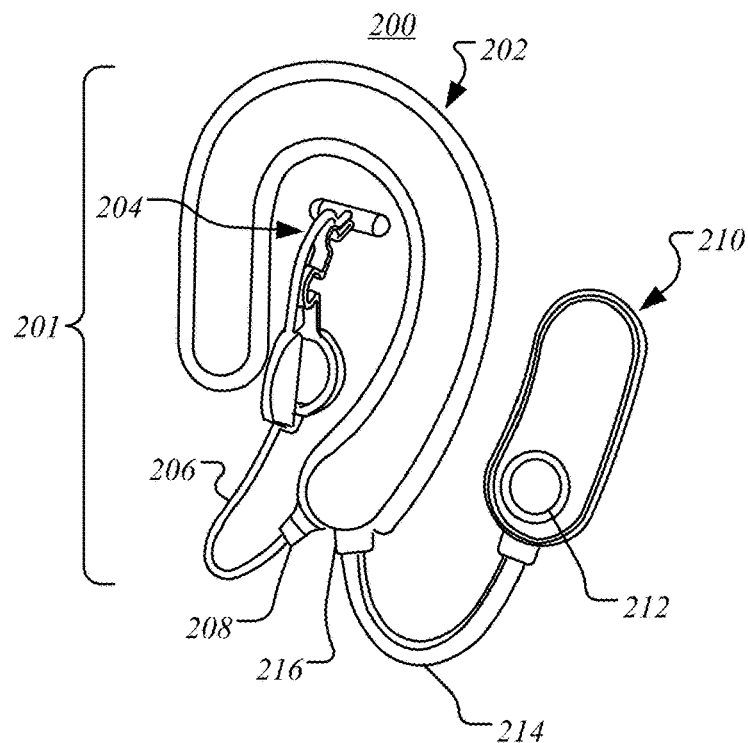
FIG. 2A is a drawing of a treatment device including an auricular component having an earpiece connected to a concha apparatus by a first connector, and a pulse generator connected to the earpiece of the auricular component by a second connector according to an example.
Figure 2B:
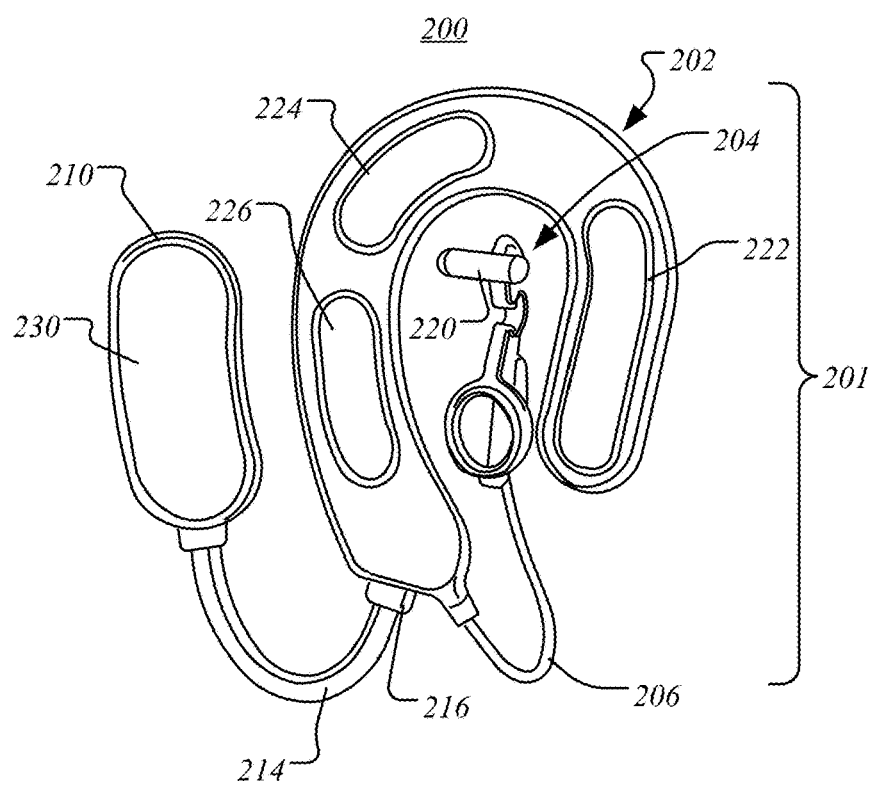
FIG. 2B is a drawing of an alternative view of the treatment device shown in FIG. 2A showing the concha apparatus including a first electrode or cymba electrode, and the earpiece including a second electrode and at least another electrode according to an example.

In some embodiments, treatment can be applied unilaterally (left or right) and yet in other embodiments a bilateral treatment may be applied, Turning to FIGS. 2A-2B, a treatment device 200 is shown including an auricular component 201 having an earpiece 202 connected to a concha apparatus 204 by a first connector 206, and a pulse generator 210 connected to the earpiece 202 of the auricular component 201 by a second connector 214 according to an example. In an example, the concha apparatus 204 includes a first electrode 220 configured to be in contact with vagal related neural structures, and the earpiece 202 includes a second electrode 222 configured to be in contact with a neural structure related to the auriculotemporal nerve and at least another electrode 224, 226 configured to be in contact with or in proximity to neural structures related to the great auricular nerve and/or its branches as well as the lesser occipital nerve and/or its branches. In an example, the pulse generator 210 can include a return electrode 230 configured to provide a return path or reference to electrodes 220-226. In another embodiment, electrodes 220-226 form pairs such that for example electrodes 220 and 226 form a pair are used to deliver bipolar stimulation; in this example a second pair could be formed by electrodes 222 and 224 such that bipolar stimulation is provided through them.

Figure 2C:
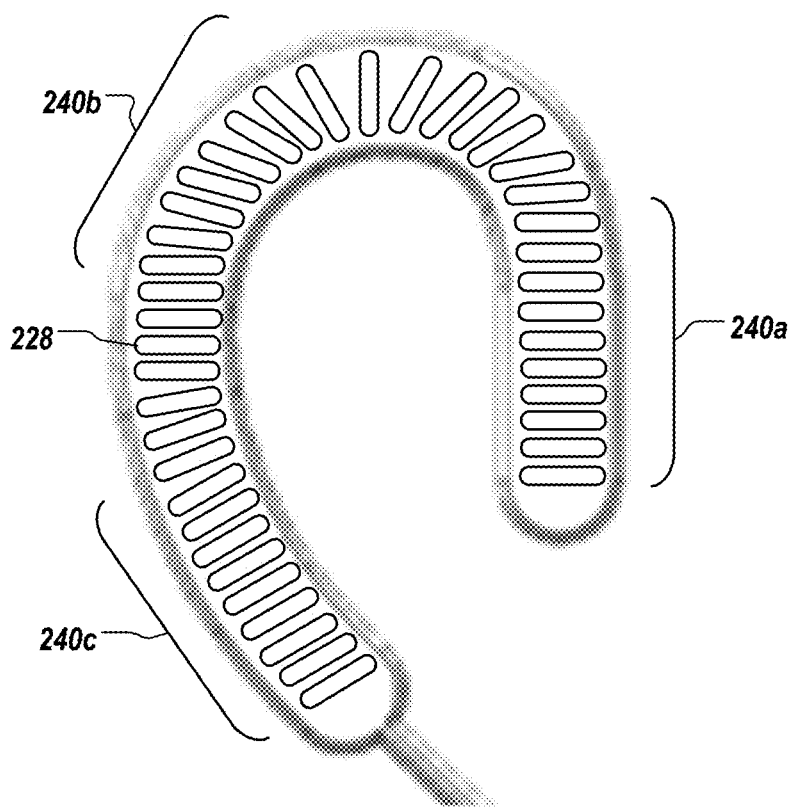
FIG. 2C is a drawing of a treatment device including a number of electrodes configured to be virtually grouped together to form one or more effective electrodes according to an example.

Turning to FIG. 2C, a treatment device can include a number of electrodes configured to be virtually grouped together to form one or more effective electrodes according to an example. In an exemplary embodiment, a treatment device can include a number of electrodes 208 that can be grouped together to form into one or more effective electrodes 240a-c. In an example, a grouping of electrodes 240a can be equivalent to electrode 222, a grouping of electrodes 240b can be equivalent to electrode 224, and a grouping of electrodes 240c can be equivalent to electrode 226.

Benefits of grouping smaller electrodes include having the ability to have multiple electrodes each one with its own independently controlled current source allows for the current to be steer providing better spatial resolution and targeting capabilities. Electrodes can also be made larger or combined such that for example in one embodiment electrodes 1206 and 1208 be combined into one large contact. In an example, the grouping of two or more electrodes (208, 224, 226) can be done using a processor such as a field-programmable gate array (FPGA) such as FPGA 1112.

In an exemplary embodiment, a treatment device includes an auricular component 201 which has a number of electrodes that are configured to be in contact with the dermis in and around the outer ear. The auricular component 201 includes at least one of the following electrodes: an electrode configured to be in contact with vagal related neural structures; for example at the cymba concha (also known as the concha of the cymba, concha cymba, and/or cymba) 204, an electrode 222 configured to be in contact with neural structure related to the auriculotemporal nerve, an electrode configured to be in contact with or in proximity to neural structures related to the great auricular nerve and/or its branches, as well as the lesser occipital nerve and/or its branches, 224 and 226. Additionally, the treatment device includes a pulse generator or controller having management software for providing the user with at least one of: customizing the therapeutic output, receiving confirmation of therapeutic delivery, and receiving and saving overall stimulation logs, diagnostics, and events.

Figure 2D:
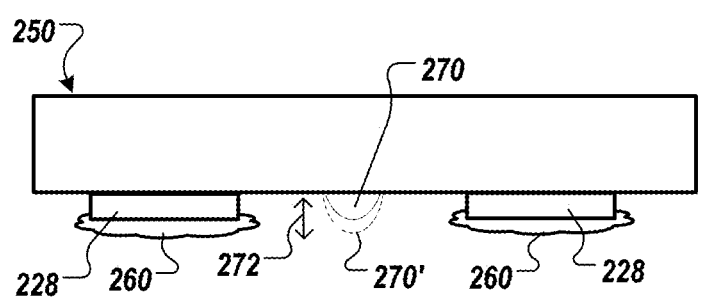
FIG. 2D is a drawing of a side view of a portion of a treatment device including haptic feedback actuators between a pair of electrodes according to an example.

In some implementations, a treatment device 250 can include one or more haptic feedback actuators 270 between a pair of electrodes 228 according to an example (FIG. 2D). In an aspect, the one or more haptic feedback actuators 270 can move 272 from a first position 270 to a second position 270' in repetitive patterns. In an example, the repetitive patterns can aid to mask sensations felt by stimulation of the electrodes. In an aspect, the one or more haptic feedback actuators 270 can be configured to isolate or electrically separate conductive shunting pathways between electrodes 228, including between portions of conductive gel 260.

Figure 3A:
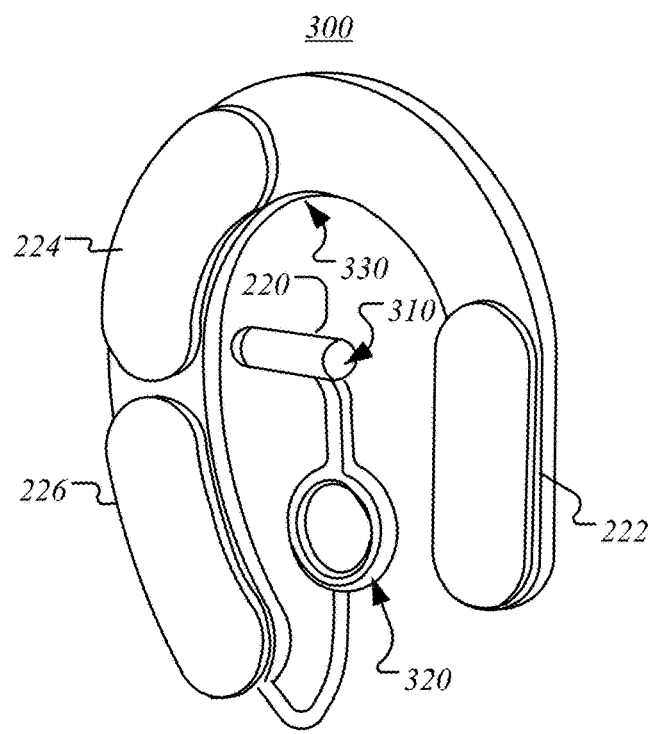
FIG. 3A is a drawing of an auricular component having an earpiece and concha apparatus with shapes configured to aid in securing the treatment device and respective electrodes to a respective ear structure according to an example.
Figure 3B:
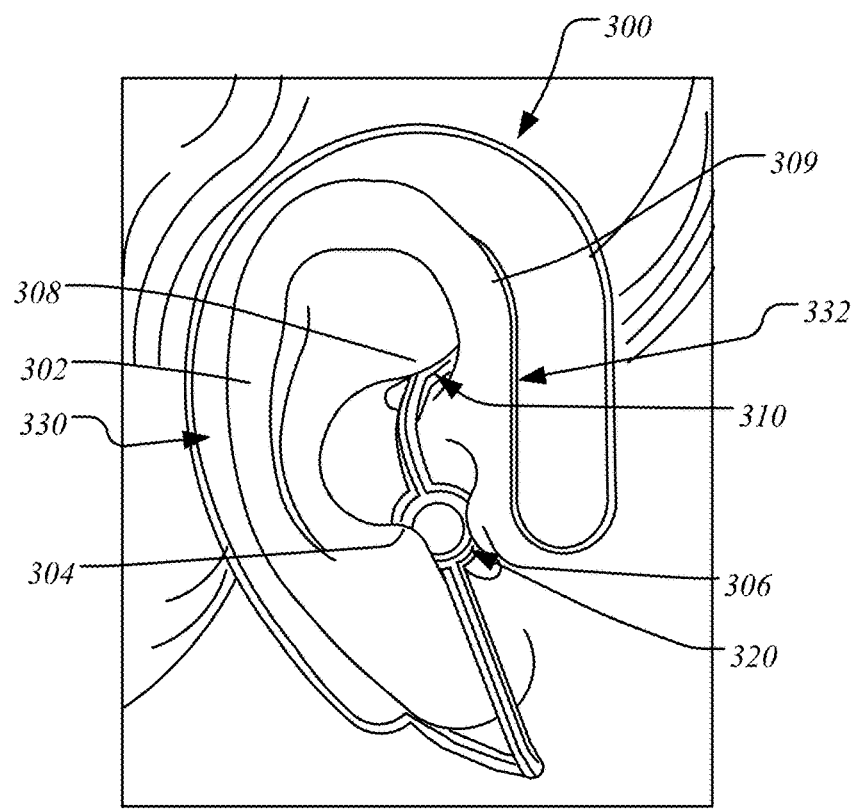
FIG. 3B is an illustration of the auricular component worn on the ear of a patient according to an example.
Figure 4A:
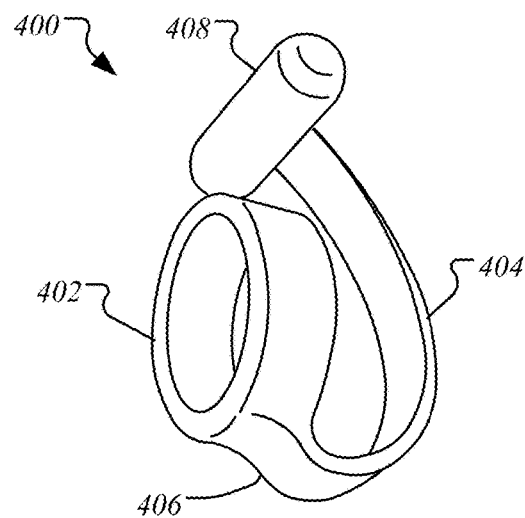
FIGS. 4A-4C are drawings of a concha apparatus having a shape configured to aid in securing the concha apparatus and respective supported electrodes to a respective ear structure according to another example.
Figures 4B, 4C:
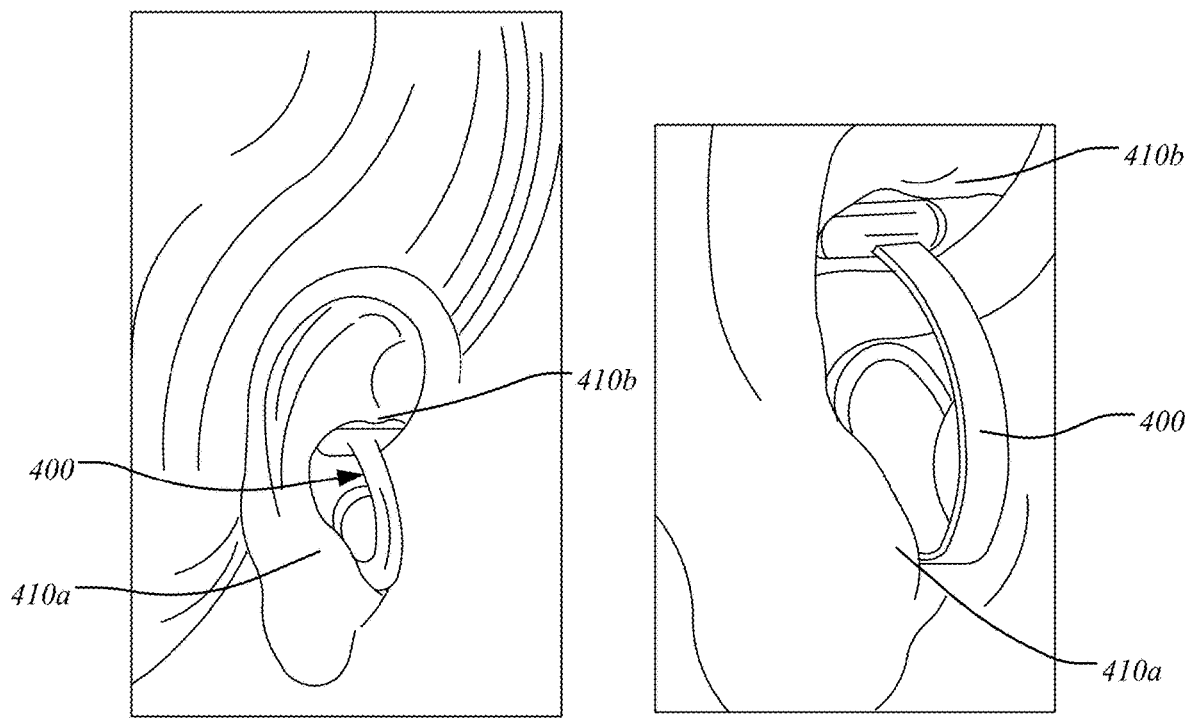

In an aspect, an auricular component can include an earpiece and concha apparatus having shapes configured to aid in securing the treatment device and the electrodes to a respective ear structure. In an exemplary embodiment, an auricular component 300 can include an earpiece and concha apparatus having shapes 310, 320, 330 configured to aid in securing the treatment device and the electrodes 220, 222, 224, 226 to a respective ear structure (See FIGS. 3A-3B). Shaped portions 310, 320, 330, 332 of the earpiece and the concha apparatus are configured to interface with structures of the ear (302, 304, 306, 308, 309) to facilitate secure placement of the electrodes for providing therapy. In another exemplary embodiment, a concha apparatus 400 can have a structural shape configured to aid in securing the concha apparatus 400 and allow for supported electrode(s) to maintain contact with a respective ear structure (See FIGS. 4A-4C). The concha apparatus 400 includes a first member 402 connected at a distal elbow 406 to an arm 404 having a second member 408 configured to fit within extrusions and notches 410*a-b* of the ear.

Figure 5A:
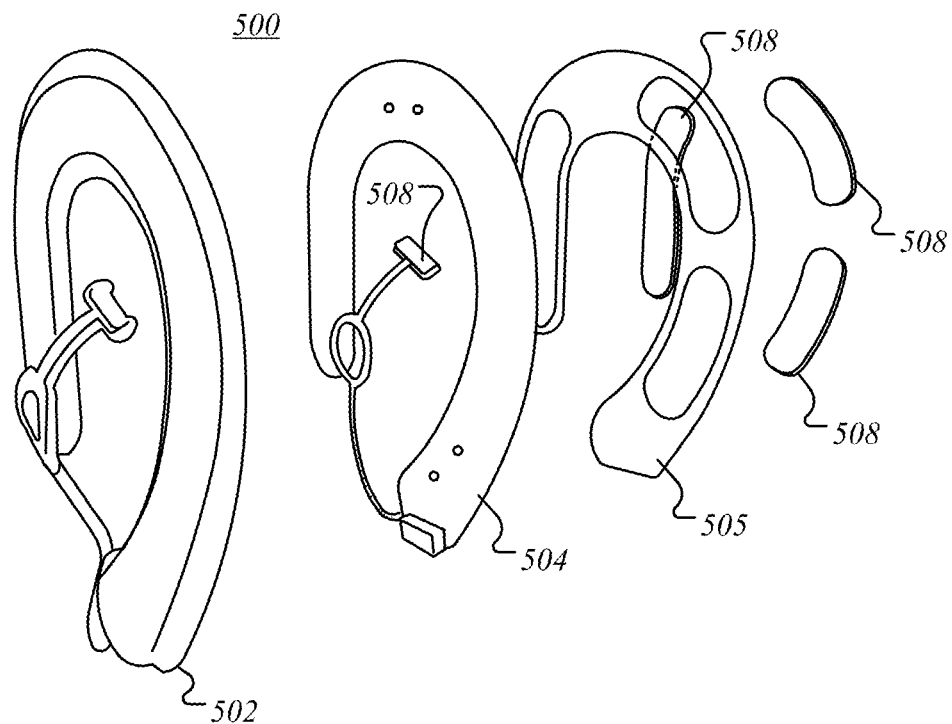
FIGS. 5A-5B are exploded views of components of the treatment device including a skin, a PCB layer, an adhesive layer composed of two elements, a skin adhesive and a number of conductive adhesive elements according to an example.
Figure 5B:
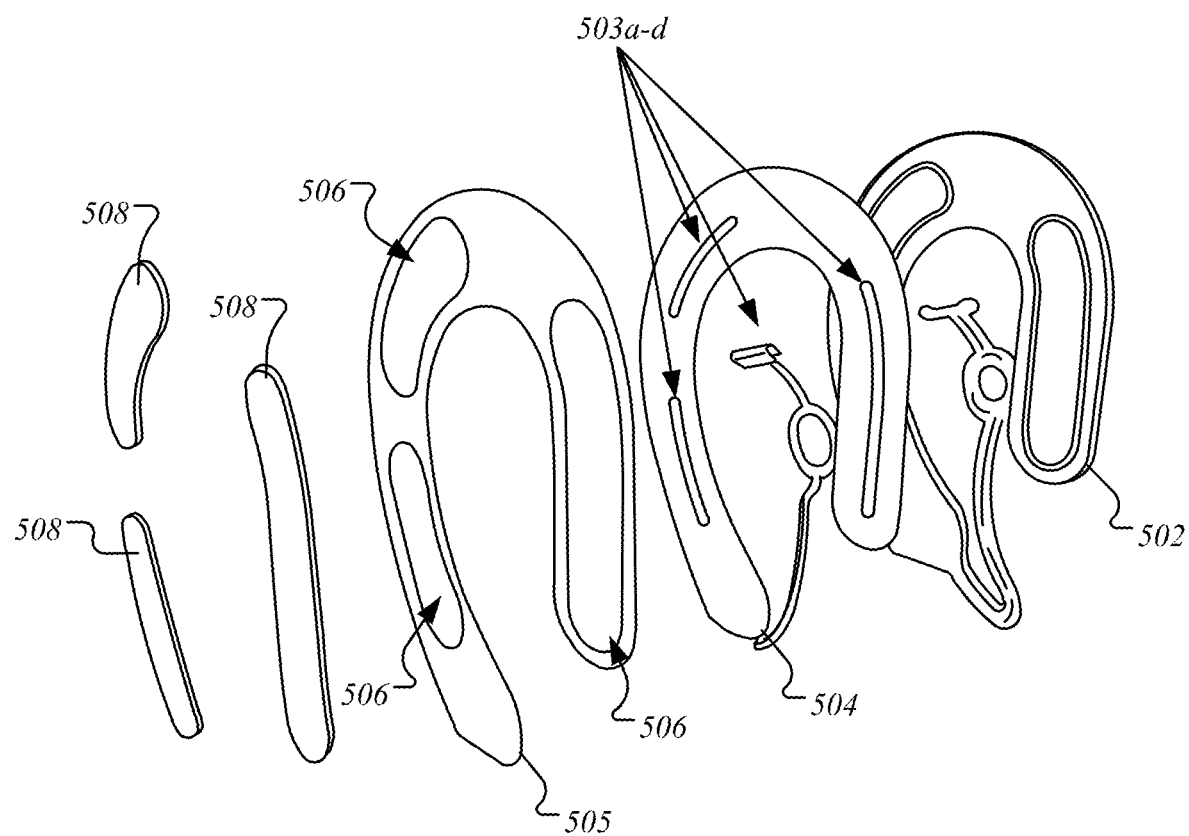

In some implementations, an earpiece assembly 500 includes a skin 502 for overlaying a PCB layer 504 having electrodes 503*a-d* (220, 222, 224, 226, 228), an adhesive layer composed of two elements, a skin adhesive 505 having corresponding apertures 506 to adhesive elements 508 configured for enhancing electrical interfacing of the electrodes 503*a-d* with the skin (See FIGS. 5A-5B). In some embodiments, the adhesive elements 508 can include a conductive hydrogel in another embodiment the hydrogel is infused with analgesic for a more comfortable stimulation. In an example, the hydrogel is on top of one or more contact surfaces on the flex PCB. In an example, the skin 502 can be made from a flexible piece or material such as silicone.

Figure 6:
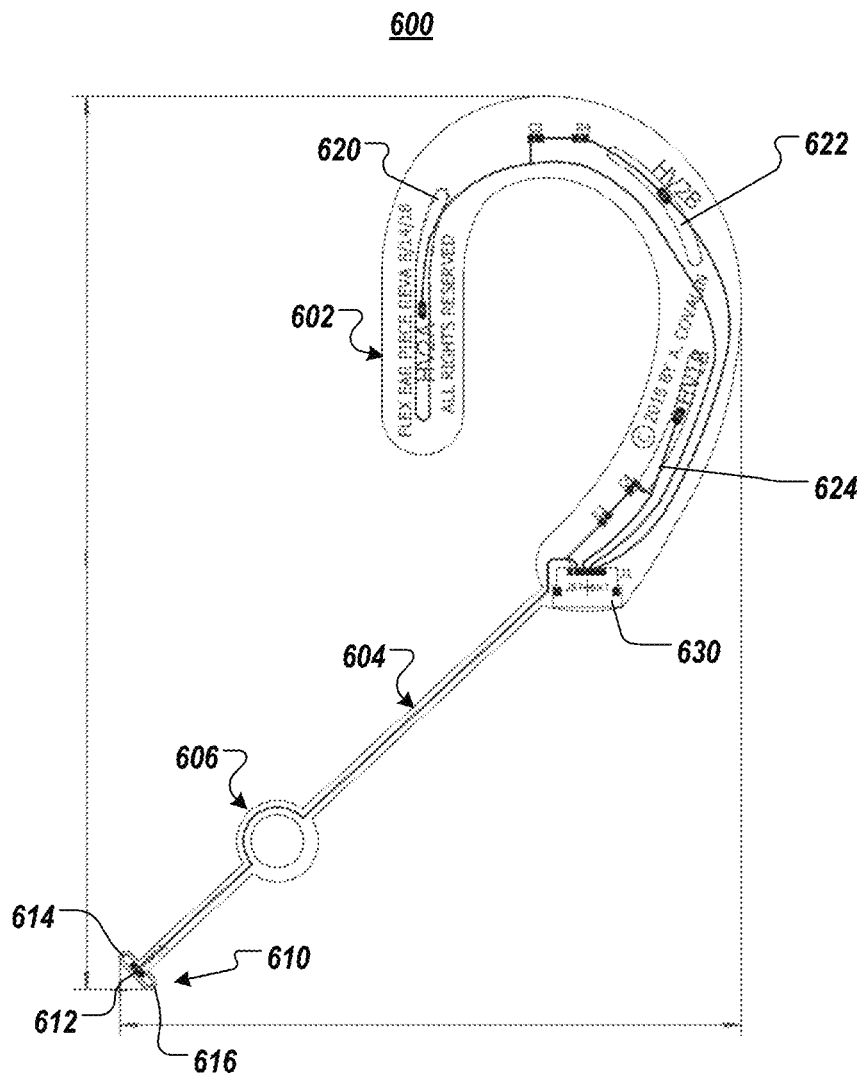
FIG. 6 is a drawing of a portion of an auricular component made from a flexible PCB according to an example.

In an example, a flexible PCB 602 can include electronic components to suppress electrical spikes as well as a component to identify and/or uniquely identify the PCB (See FIG. 6). Exposed conductive surfaces 612, 620, 622, 624 on the PCB 602 serve as contact point to connect the hydrogels 508 to the PCB 602. The PCB 602 extends forming a cable-like structure 604 to integrate the cymba component 610 of the electrode 220 in contact with nerve branches related to vagal nerve structures 204 without the need for soldering and/or connecting the electrode 220 during assembly. In one embodiment, the cable-like structure forms an anchoring structure 606 which sits inside portions of the ear. In this example, PCB 602 connects to the pulse generator 210 via a slim keyed connector 630. In another embodiment, more than one electrode can be located on the cymba component 610. In this case, additional components can be added to the PCB 602 to accommodate additional electrodes including additional traces on the PCB 602. In an example, additional connections could extend along the cable-like structure 604 and connector 630 can have additional contact pins. In another embodiment, an analog multiplexor could be added to control and/or direct or re-direct the stimulation pulses towards a desired electrode and/or set of electrodes.

Figure 7A:
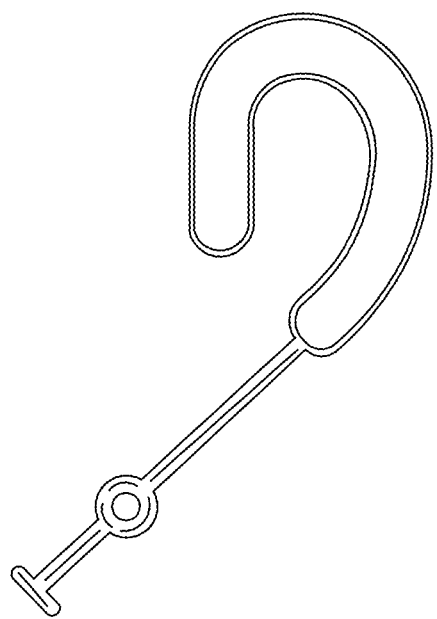
FIG. 7A-7C are drawings of the flexible PCB encapsulated in a protective covering according to an example.
Figure 7B:
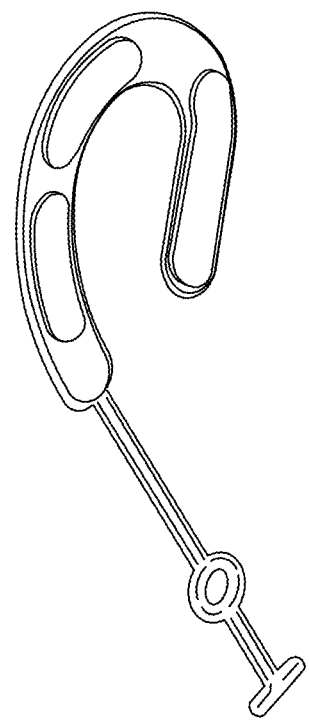
Figure 7C:
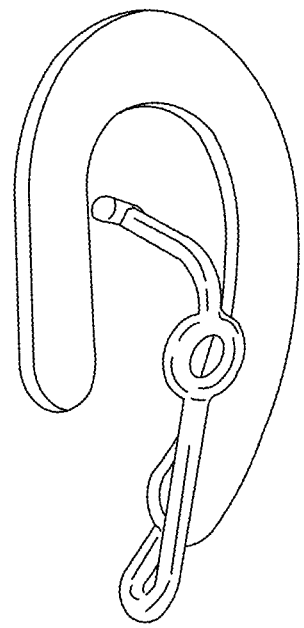

In an example, the flexible PCB can be encapsulated in a protective covering as shown in FIGS. 7A-7C. The protective covering can be made from a flexible material such as silicone. The protective covering can be an encapsulation that may have different thickness and densities in order to provide comfort to the touch and robustness and protection to the PCB. The encapsulation is done with at least one material. In some embodiments, the encapsulation is done at least in using one mold and at least one molding step.

Figure 8A:
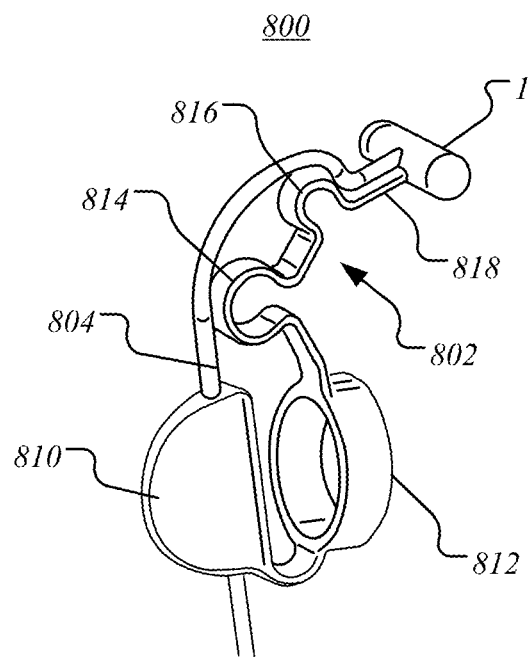
FIGS. 8A-8B are drawings of a structural-loaded component configured to facilitate placement of the cymba electrode according to an example.
Figure 8B:
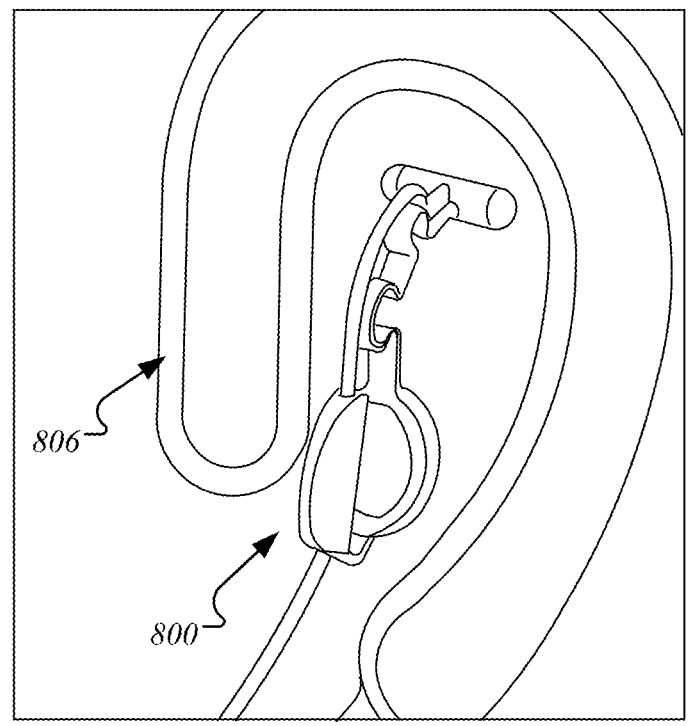

In an aspect, a concha apparatus can include a component for facilitating placement of the cymba electrode to portions of the ear. In an exemplary embodiment, a concha apparatus can include a structural-loaded component 800 which facilitates the placement of the cymba electrode 204 to portions of the ear (See FIG. 8A-8B). Spring loading has the added advantage that it is self-fitting allowing a secure and comfortable fit for different ear sizes. The presented shape (i.e., omega shape 814, 816) has the added advantage that it can be made with metal and non-metal materials. Other suitable shapes may be fabricated to allow a structural-loaded action using metal and/or non-metal materials or a combination of both metal and non-metal materials. In this example, the cable-like structure 604 after encapsulation with, for example, silicone 804 is routed such that the PCB 602 does not need to incorporate the anchoring structure 606. In this case, the cable-like structure 804 goes through a handle-like feature 810 that can be utilized by the user to handle and placed the component 800 on the user's ear.

An anchoring structure 812 is placed in the ear and the electrode in contact with nerve branches related to vagal nerve structures 204 is placed in the cymba. The use of an anchoring structure outside the ear canal instead of a part going into the ear canal for the placement serves three purposes, comfort, functionally (it does not block sound) and, safety (minimal risk of having a loose part going into the ear canal). Aside from the handle 810 and anchoring structure 812, component 800 has two omega-like structures 814, 816 having a structural-loaded effect, a flat structure 802 connecting structural-loaded components 814 and 816 and a flat structure 818 attaching electrode 204 to component 800. Structural-loaded structure 814 helps in directing the rest of component 800 (i.e. 802, 816, 818, 204) medially (i.e. towards the user's head) while the structural-loaded structure 816 helps in directing electrode 204 cranially inside the cymba crevice (i.e. towards the upper portion of the cymba crevice).

Figure 9B:
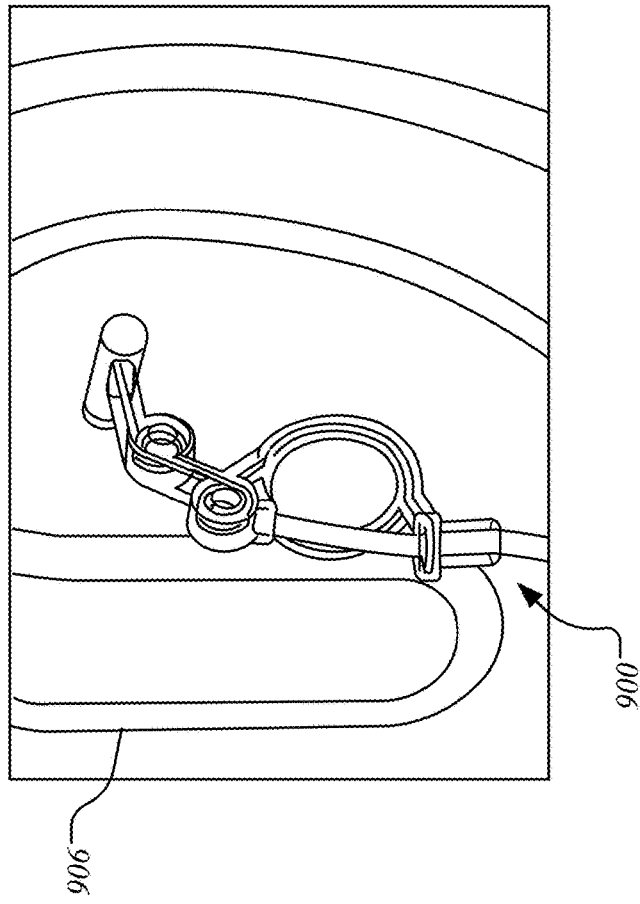
FIGS. 9A-9C are drawings of a spring-loaded component configured to facilitate placement of the cymba electrode according to an example.
Figure 9C:
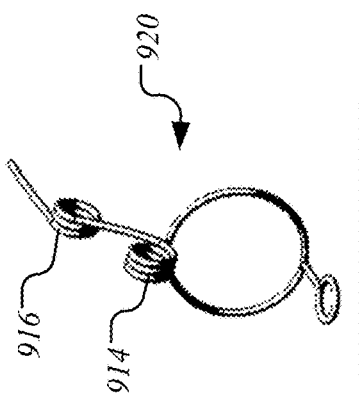
Figure 9A:
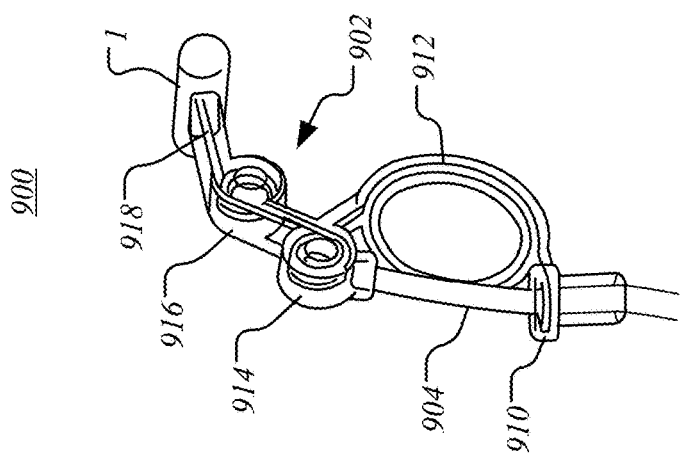

In an exemplary embodiment, a concha apparatus can include a spring-loaded component 900 which facilitates the placement of the cymba electrode 204 on the user's ear. (See FIG. 9A-9B). Spring loading has the added advantage that it is self-fitting allowing a secure and comfortable fit for different ear sizes. The presented shape (i.e. classic spring) is usually fabricated with metallic materials. Other suitable shapes may be fabricated to allow a spring-loaded action using metallic materials, and/or non-metal materials or a combination of both metal and non-metal materials. In this example, the cable-like structure 604 after encapsulation with, for example, silicone 904 is routed such that the PCB 602 does not need to incorporate the anchoring structure 606. In this case, the cable-like structure 904 goes through holder 910 which can be utilized by the user to handle and placed the component 900 on the user's ear. An anchoring structure 912 is placed in the ear and the electrode 204 in contact with nerve branches related to vagal nerve structures is placed in the cymba. The use of an anchoring structure outside the ear canal instead of a part going into the ear canal for the placement serves three purposes, comfort, functionally (it does not block sound) and, safety (minimal risk of having a loose part going into the ear canal). Aside from the handle 910 and anchoring structure 912, component 900 has two springs 914, 916, a flat structure 902 connecting the two springs 914 and 916 and a flat structure 918 attaching electrode 204 to component 900. Spring 914 helps in directing the rest of component 900 (i.e., 902, 916, 918, 204) medially (i.e., towards the user's head) while spring 916 helps in directing electrode 204 cranially inside the cymba crevice (i.e. towards the upper portion of the cymba crevice). In some embodiments, a single wire 920 is shaped such that components 910, 912, 914, 916, and 918 are formed (See FIG. 9C). In some embodiments, the wire is encapsulated into a comfortable-to-the-touch and flexible material (e.g., silicone). In some embodiments, holder 910 is longer, for example it could bridge over the entire anchoring structure 912 for a more functional and comfortable handling.

In some implementations, the pulse generator 210 includes a battery, circuitry configured to produce therapy stimulation in communication with the electrodes of the auricular component 201. In some embodiments, the pulse generator includes at least one antenna configured to receive programming instructions encoding stimulation parameters. In an aspect, the system is rechargeable to allow for long-term use.

In an exemplary embodiment, the auricular component 201 is connected to an electrical pulse generator 210 which produces the therapy stimulation going to the electrodes on the auricular component 201. In one embodiment, the pulse generator 210 is co-located in close proximity with the auricle of the patient.

In another embodiment, the pulse generator 210 is placed on the body of the user, for example on the pectoral region just below the clavicle. In another embodiment, the pulse generator 210 can be clipped to the user's clothing or carried in the user's trousers pocket or in a specially designed pouch. In one embodiment, the pulse generator 210 is controlled via remote control for example using a peripheral device such as a mobile device, a tablet, and a personal computer. In an aspect, other system components are configured to be controlled by an application on the peripheral device. In one embodiment, data is exchanged via a computing cloud with third parties for example healthcare professionals and/or healthcare providers. (See FIGS. 10A-10C)

Figure 10A:
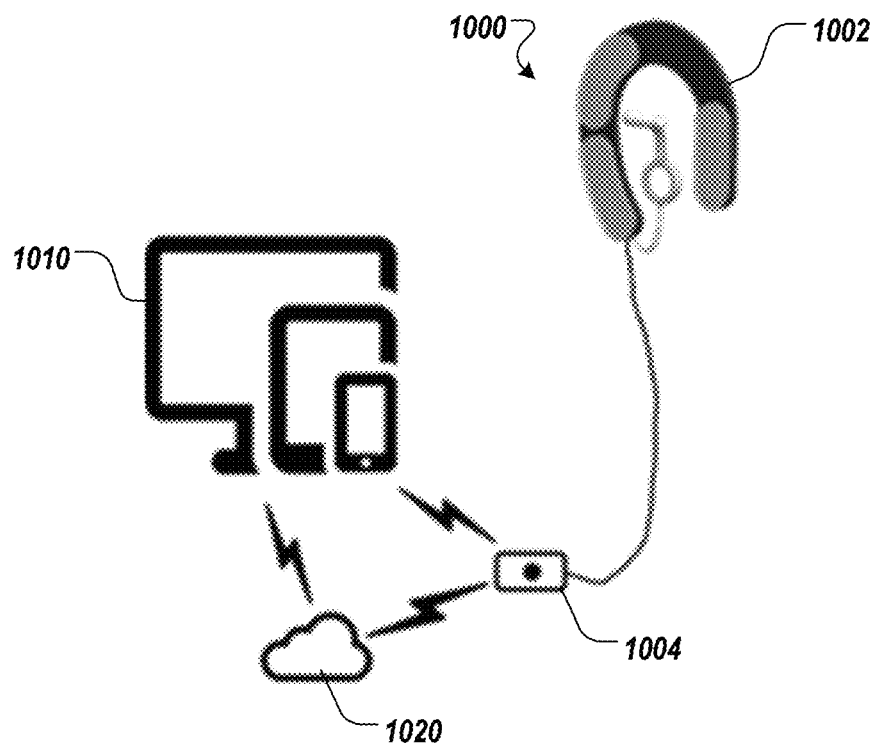
FIGS. 10A-10C are drawings of a system including the treatment device in communication with third parties through a computing cloud and/or a peripheral device according to an example.
Figure 10B:
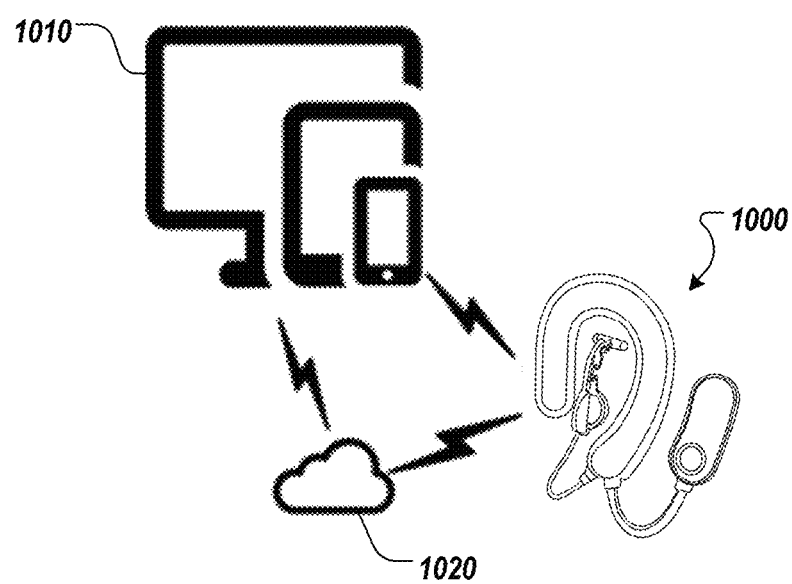
Figure 10C:
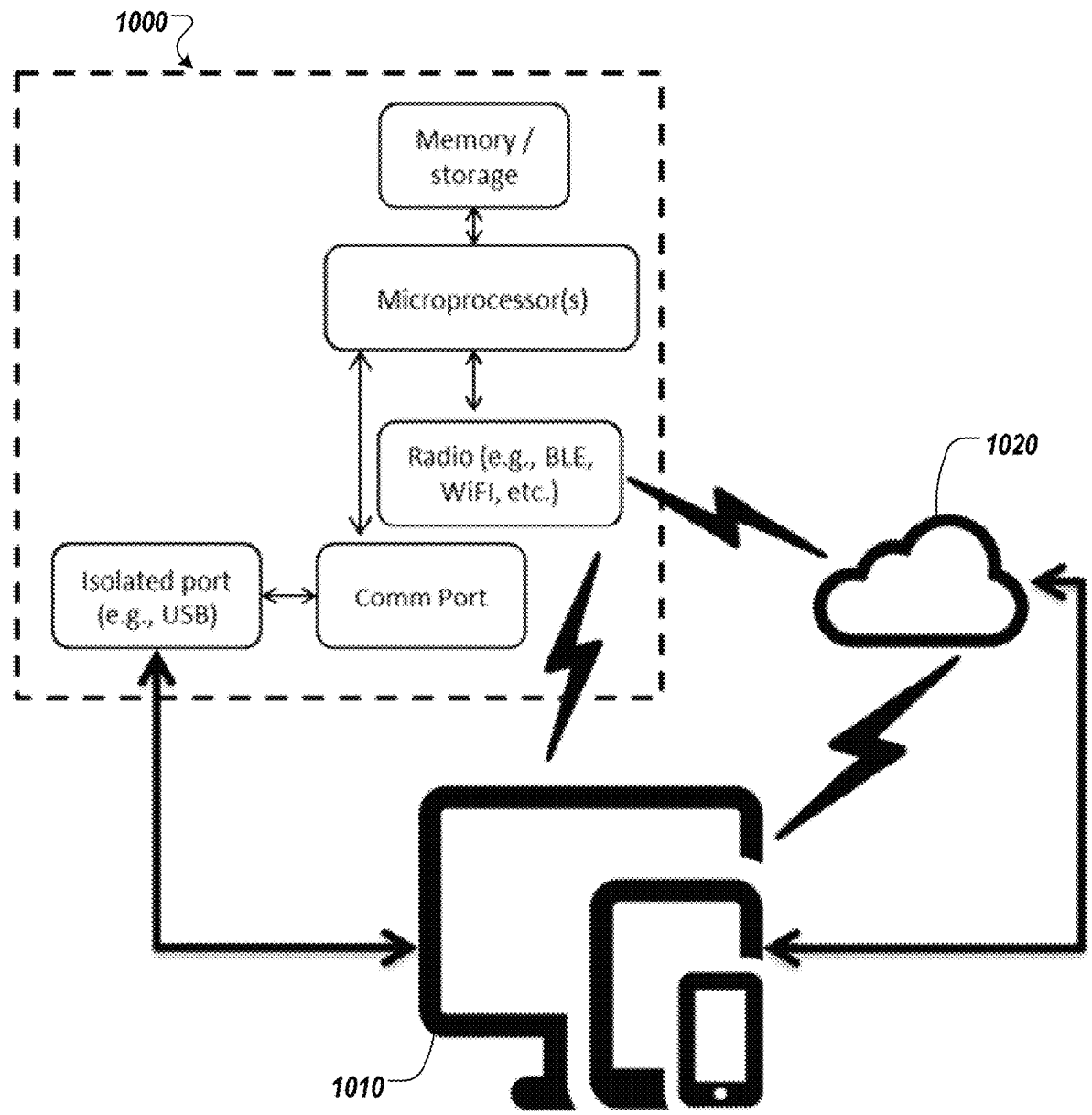

Turning to FIGS. 10A-10C, a treatment system can include a treatment device 1000 in communication with third parties through a computing cloud 1020 and/or a peripheral device 1010 according to an example. In this example, the treatment device 1000 is shown including an auricular component 1002 connected via a wire to a pulse generator 1004, and the pulse generator 1004 is wirelessly connected to the peripheral device 1010. Examples of peripheral devices 1010 includes a personal computer, a tablet, a phone as well as any other suitable device including a remote server via the cloud 1020. In an example, the peripheral device 1010 is also wirelessly connected to a remote server via the cloud 1020. Wireless connections can be accomplished via any at least one available wireless technology, for example, BlueTooth Classic, BlueTooth Low Energy, ZigBee, WiFi or similar technology.

Portions of the treatment system and the treatment device can be in direct or indirect communication with a remote server or cloud 1020 with third parties. In this example, the pulse generator 210 is included in the auricular component 1002 that is, they are co-located thus the need for and extension cable to connect them is not necessary. The auricular component and pulse generator 210 are wirelessly connected to an electronic device (for example a personal computer, a tablet or a phone) and/or to a remote server via the cloud 1020. In turn the electronic device is also wirelessly connected to a remote server via the cloud 1020. Wireless connections can be accomplished via any at least one available wireless technology, for example, BlueTooth Classic, BlueTooth Low Energy, ZigBee, WiFi or similar technology. As shown in FIG. 10C, different communication components of the treatment device 1000 can be in communication with the peripheral device 1010 and the remote server or cloud 1020. For example, an isolated port on the treatment device 1000 can be in wired communication with the peripheral device 1010, a wireless radio of the treatment device 1000 can be in wireless communication with the peripheral device 1010 or the remote server or cloud 1020.

Figure 11:
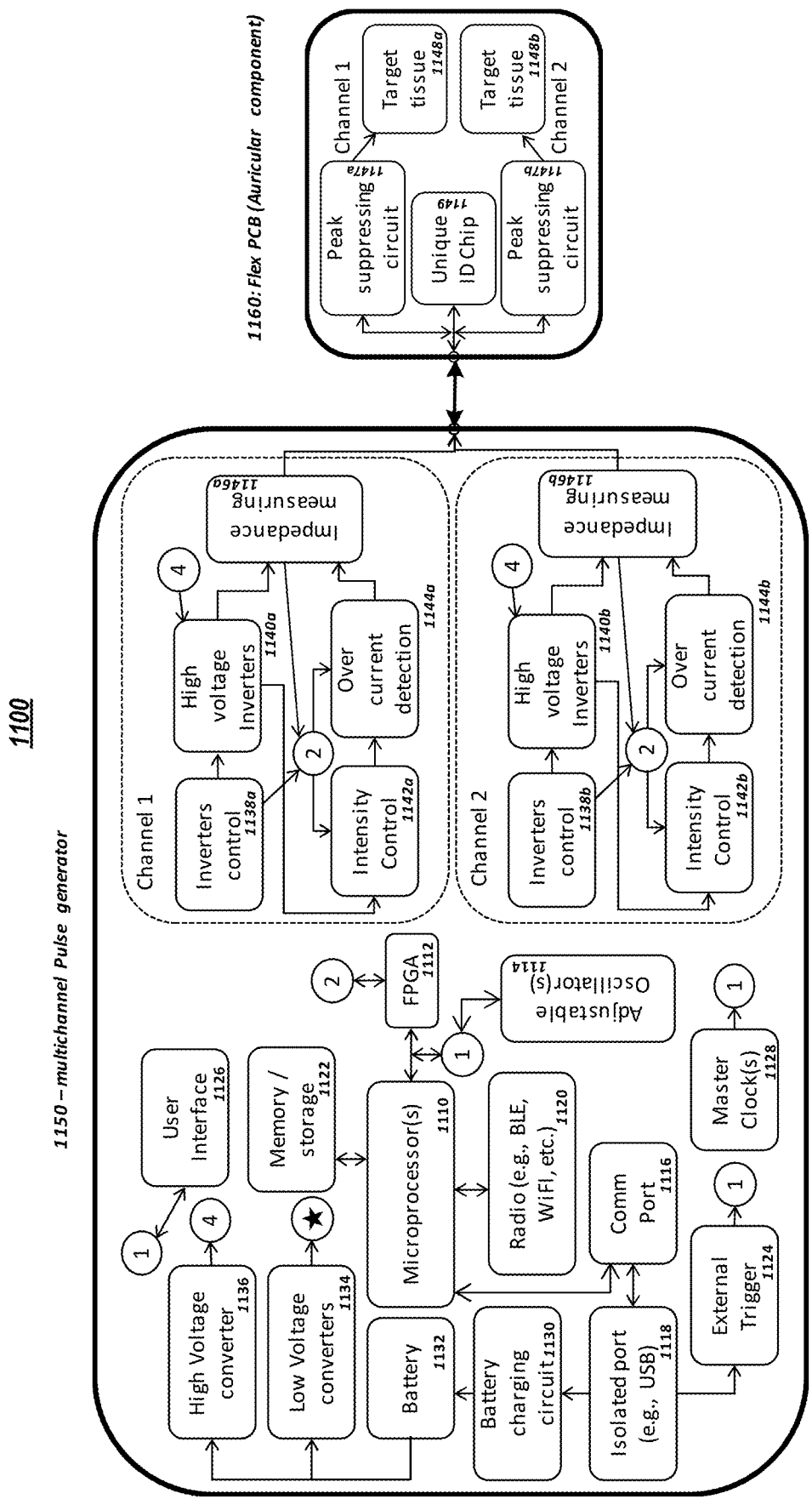
FIG. 11 is a drawing of a schematic of components of a pulse generator in communication with components of the flexible PCB of the auricular component according to an example.

Turning to FIG. 11, a schematic 1100 of components of a pulse generator 1150 in communication with components of the flexible PCB 1160 of the auricular component is shown according to an example. The multichannel pulse generator circuit 1150 has at least one microcontroller or a microprocessor 1110 with at least one core. When multiple microcontrollers or multiple cores are present, for example one controls the radio 1120 and other core(s) are dedicated to control the therapy. In one embodiment, a low power FPGA 1112 is also available such that the microcontroller 1110 goes into a low power mode as much as possible while the FPGA 1112 controls therapy delivery.

In some embodiments, an inverter circuit 1140 is used to generate biphasic/bipolar pulses. In some embodiments, one inverter circuit is use per channel, while in other embodiment, a single inverter is used for multiple channels. In one embodiment, each channel targets a different anatomical area 1148. A high voltage compliance (e.g., >50V, in other embodiments >70V, and yet in others >90V) is needed to ensure there is enough margin on the electrical potential to generate current demanded by the intensity control 1142. In order to enhance safety, in some embodiments an over current detection circuit 1144 is present. In one embodiment an impedance measuring circuit is present 1146, such that impedance can be tracked over time and to identify when the electrodes are not in contact or in good contact with the skin or if the cable is disconnected, or if the electrodes have deteriorated or are defective. Monitoring impedance over time provides the added advantage that the condition of the contact electrode can be followed; thus allowing the circuit to alert the user when the contact electrodes are close to their end of life of no longer viable.

In some embodiments, an isolated port 1118, such as a USB is used to charge the battery, and to communicate with the microcontroller(s) 1110. The communication can be both ways, such that instructions or entire new code can be uploaded to the microcontroller(s) 1110 and to download information stored in the memory 1122. In some embodiments, memory 1122 can be added to the circuit as an external CHIP, while in other embodiments, the memory 1122 can be internal to the microcontroller(s) 1110. In some embodiments, the FPGA 1112 may also have internal memory. In some embodiments, an external trigger circuit 1124 is included, such that the stimulation can be started and/or stopped via an external signal. In some embodiments, the external trigger signal can be passed through the isolated port 1118; in yet other embodiments a modify USB configuration (i.e., not using the standard USB pin configuration) can be used to pass the trigger signal. Using a modify USB configuration will force a custom USB cable to be used thus ensuring that an external trigger cannot be done by mistake using an off-the-shelf USB cable.

In some embodiments, a hardware user interface is used to interact with the circuit 1126. In an example, the user interface can comprise of buttons, LEDs, buzzers, and/or a display, or a combination of any of them.

In some embodiments, an external master clock 1128 is used to drive the microcontroller(s) 1110 and/or the FPGA 1112, in other embodiments the clock(s) can be internal or integrated or co-packaged with the microcontroller(s) 1110 and/or the FPGA 1112. In some embodiments, one or more oscillators, including in some cases adjustable oscillators 1114 are used to set pulse parameters such as for example, frequency and/or pulse width.

In some embodiments, the auricular component 1160 is made from a thin flex PCB, such that it is light weight and can be easily bent to accommodate different anatomies. In some embodiments, the auricular circuit 1160 has more than one channel. In one embodiment, each channel includes a peak suppressing circuit 1147 and electrodes 1148 to contact the skin at the location of the target tissue. In some embodiments, the auricular circuit 1160 includes a unique chip identifier or unique ID chip 1149. The unique ID chip can be used to track usage as well as to prevent other no authorized circuits to be connected to the multichannel pulse generator 1150. At least one auricular circuit 1160 is connected to the multichannel pulse generator 1150.

Figure 14D:
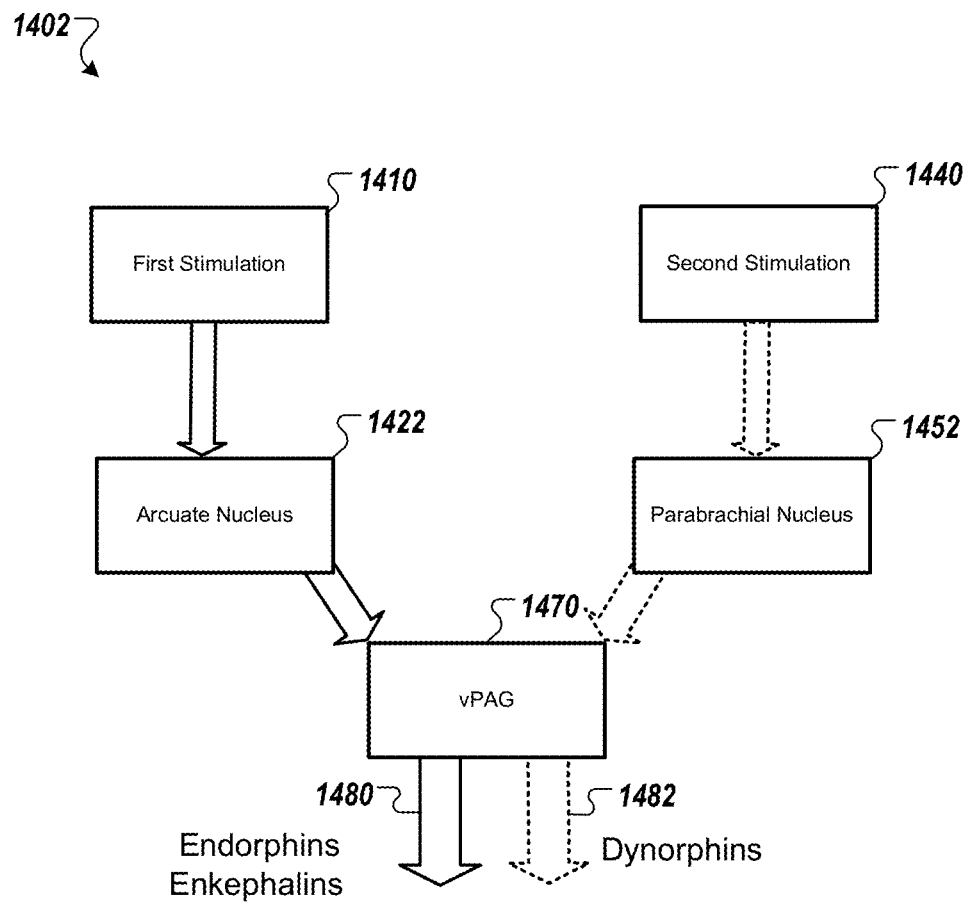
FIG. 14D is a flow chart of a method for providing therapy including providing a first stimulation at a first tissue location such that neural activity at the arcuate nucleus of the hypothalamus (ARC) is modulated such that it stimulates the Periaqueductal Gray Area (PAG) for modulating a first release of enkephalins and/or endorphins, and a second stimulation at a second tissue location such that neural activity at the Parabrachial Nucleus (PbN) is modulated such that it also stimulates the Periaqueductal Grey Area (PAG) for modulating a second release of a dynorphins, according to an example.

Turning to FIGS. 14A-14D, a method 1400 is disclosed for providing therapy including providing a first stimulation 1410 at a first tissue location configured to stimulate a first pathway 1420 for modulating a first release 1430 of at least one first endogenous peptide and a second stimulation 1440 at a second tissue location configured to stimulate a second pathway 1450 for modulating a second release 1460 of a second endogenous peptide according to an example. Examples of target pathways and structures for stimulation of the first tissue location include those modulating activity at/on the auricular branch of the vagus nerve, the lesser occipital nerve, the great auricular nerve, and the arcuate nucleus (FIG. 14B). Examples of target pathways and structures for stimulation of the second tissue location include those modulating activity at/on the auriculotemporal nerve, the lesser occipital nerve, the great auricular nerve, and the parabrachial nucleus (FIG. 14C).

FIG. 14D shows a flow chart of a method 1402 for providing therapy including providing a first stimulation such that neural activity at the arcuate nucleus of the hypothalamus (ARC) is modulated such that it stimulates the Periaqueductal Gray Area (PAG) for modulating a first release of enkephalins and/or endorphins such that neural activity at the Parabrachial Nucleus (PbN) is modulated such that it also stimulates the Periaqueductal Grey Area (PAG) for modulating a second release of a dynorphins according to an example.

In an aspect, the stimulation targets specific neural targets in a local manner using bipolar stimulation. In an aspect, the system can be programmed for optimal therapy according to the needs of individual users including custom stimulation frequency, custom pulse width, custom stim intensity (amplitude), independently controlled stimulation channels. In some implementations, the treatment is configured to abate withdrawal symptoms including pain. In an aspect, pain control is due to modulation of endorphin, enkephalins, and/or dynorphins output in opioid related systems. In an example, the therapy can be provided during surgery, and/or post-surgery to reduce dependency of pain killer medications, including opioids, up to not needing medication at all.

Figure 12:
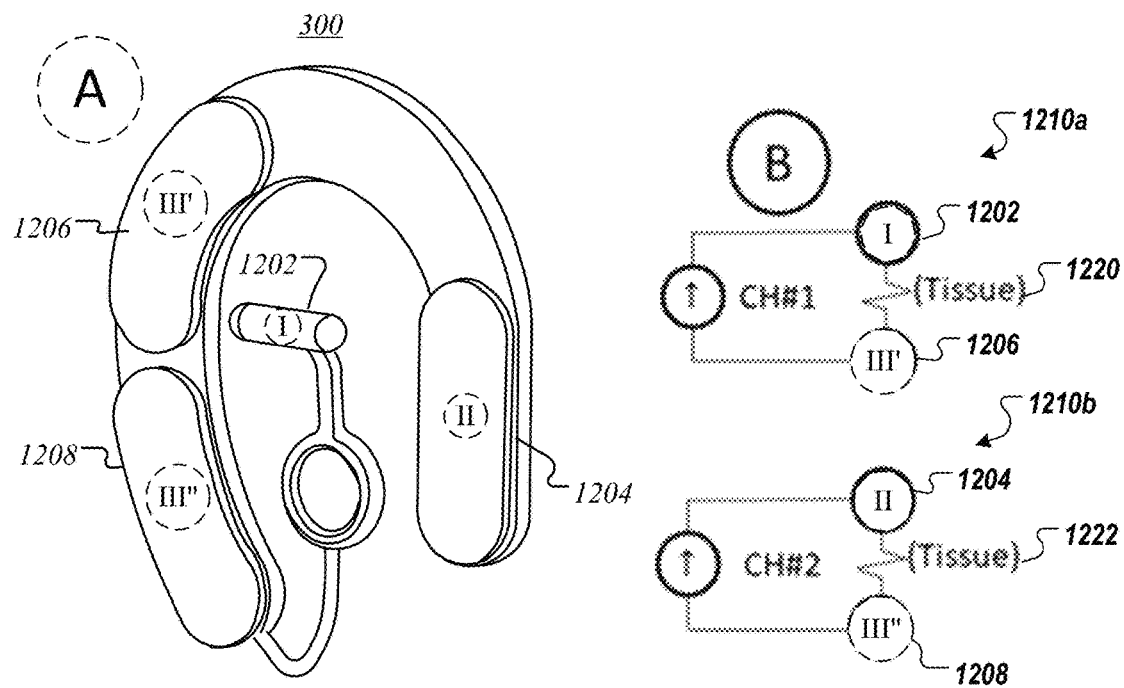
FIG. 12 is a drawing of an electrode configuration and equivalent circuit for providing therapy according to an example.

Turning to FIG. 12, an electrode configuration of an auricular component 1200 and equivalent circuits 1210*a-b* for providing therapy is shown according to an example. The auricular component 1200 is shown having electrodes 1202 (220), 1204 (222), 1206 (224), and 1208 (226) configured to form corresponding circuits 1210*a-b* according to an example. In an example, equivalent circuit 1210*a* is formed by electrode 1202 and electrode 1206 which are configured to stimulate tissue portion 1220. In this example, tissue portion 1220 is configured to target the cymba conchae region which is enervated by branches of the auricular branch of the vagus nerve and the region behind the ear which is enervated by branches of the great auricular nerve and branches of the lesser occipital nerve. In an example, equivalent circuit 1210*b* is formed by electrode 1204 and electrode 1208 which are configured to stimulate tissue portion 1222. In this example, tissue portion 1222 is configured to target the region rostral to the ear which is enervated by the Auriculotemporal nerve as well as the region behind the ear which is enervated by branches of the great auricular nerve and branches of the lesser occipital nerve.

In an example, the tissue portion 1220 can be the concha which is stimulated at approximately 5 Hz. In an example, the tissue portion 1220 can be the trigeminal nerve which is stimulated at approximately 100 Hz.

In an example, equivalent circuit 1210*a* is stimulated by a first channel and equivalent circuit 1210*b* is stimulated by a second channel.

Figure 13:
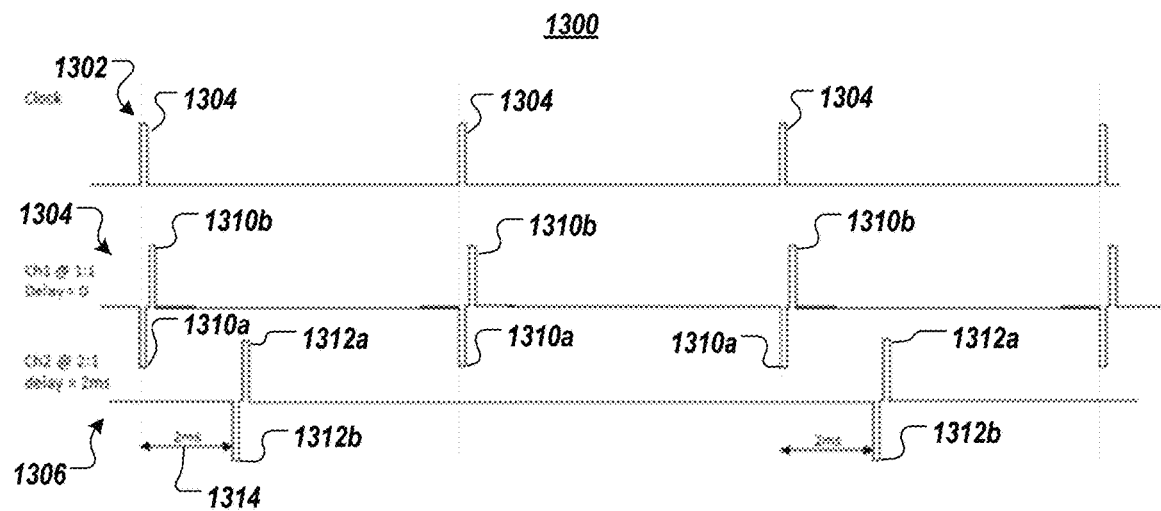
FIG. 13 is a drawing of a method for triggering multiple channels using a single clock according to an example.

FIG. 13 is a drawing of a method 1300 for triggering multiple channels 1304, 1306 using a master clock 1302 according to an example. In an exemplary embodiment, the clock 1302 triggers pulses 1304 at a predetermined clock frequency. In an example, a first channel 1304 can be configured to trigger stimulation 1310*a-b* of equivalent circuit 1210*a* and a second channel 1306 can be configured to trigger stimulation 1312*a-b* of equivalent circuit 1210*b*.

In an example, the triggering can be reversed where equivalent circuit 1210*b* is triggered before equivalent circuit 1210*a*.

In an example, stimulation 1310*a* is configured to be triggered by every pulse of the master clock; i.e., at a 1-to-1 ratio. In an example, stimulation 1310*b* is configured to be triggered following a specific time interval after the pulse in stimulation 1310*a* ends. In an example, stimulation 1312*b* is configured to be triggered every two pulses of the master clock; i.e., at a 2-to-1 ratio with the master clock. However, the triggering of stimulation 1312*b* occurs after a specific time delay after the master clock pulse 1314. In an example, stimulation 1312*a* is configured to be triggered following a specific time interval after the pulse in stimulation 1312*b* ends. In an example, stimulation 1310*a* is offset by stimulation 1312*a* by a synchronous delay 1314. In an example, the synchronous delay 1314 is preferably 2 ms and can be as little as zero (making both channels to trigger simultaneously depending on the master clock ratio for each channel) and as much as the master clock period less the combine duration of stimulation 1312*b* and 1312*a* plus the time interval between them. In some embodiments this delay can amount to 10 ms.

In some implementations, the equivalent circuits are synchronized using a master clock counter and a register per channel. By setting each register to a number of master clock pulses to trigger the respective channel, each channel is configured to be triggered when the channel register value equals the master clock pulses. Subsequently, the counter for each channel is reset after the channel is triggered. In an example, using a 6 bit counter and a 6 bit register, the trigger frequency can be as high as the master clock frequency (1:1) and as low as 1/64 of the clock frequency (64:1).

In one embodiment, the stimulation patterns are such that stimulating frequencies are not the same in all electrodes. In one embodiment, a stimulation frequency is varied between 2 Hz and 100 Hz such that different endogenously produced opioid receptor agonist are released (e.g., Mu, Delta, Kappa, nociception opioid receptor agonist). In yet another embodiment, the pulse width can be adjusted from between 20 and 1000 microseconds to further allow therapy customization.

In one embodiment, different stimulation frequencies are used at the different electrodes. For example, a first or low frequency of between 1 to 5, or 5 to 10, or 10 to 15, or 15 to 20, or 20 to 25, or 25 to 30 Hz is used at cymba electrode 204, while a second of high frequency of between 70 to 75, or 75 to 80, or 80 to 85, or 85 to 90, or 90 to 95, or 95 to 100, or 100 to 105, or 105 to 110, or 110 to 115, or 115 to 120, or 120 to 125, or 125 to 130, or 130 to 135, or 135 to 140, or 140 to 145, or 145 to 150 Hz is used at the auriculotemporal electrode 222. In other embodiments, a third or midrange frequency of between 30 to 35 or 35 to 40 or 40 to 45 or 45 to 50 or 50 to 55 or 55 to 60 or 60 to 65 or 65 to 70 Hz can be used at either electrode.

In yet another embodiment, a low or midrange frequency can be used in the cymba electrode 204 while high frequency is used at the auriculotemporal electrode 222. In other embodiment, a high frequency can be use at the cymba electrode 204 while a Low frequency can be used at the auriculotemporal electrode 222. In yet other embodiments, different combinations of high, midrange and low frequency can be used at either the cymba electrode 204, the auriculotemporal electrode 222, and/or the great auricular nerve and lesser occipital nerve electrodes 224, 226.

Different combination of pulse widths can be used at each electrode. First or short pulse widths of between 10 to 20, or 20 to 30, or 30 to 40, or 40 to 50 microseconds, second or low Midrange pulse widths of between 50 to 70, or 70 to 90, or 90 to 110, or 110 to 130, or 130 to 150, or 150 to 170, or 170 to 190, or 190 to 210, or 210 to 230, or 230 to 250 microseconds, third or high Midrange pulse widths of between 250 to 270, or 270 to 290, or 290 to 310, or 310 to 330, or 330 to 350, or 350 to 370, or 370 to 390, or 390 to 410, or 410 to 430, or 430 to 450, or 450 to 470, or 470 to 490, or 490 to 510, or 510 to 530, or 530 to 550 microseconds, fourth or long pulse widths of between 550 to 600, or 600 to 650, or 650 to 700, or 700 to 750, or 750 to 800, or 800 to 850, or 850 to 900, or 900 to 950, or 950 to 1000 microseconds. Different embodiments can use different ranges of pulse widths at one or more of the electrodes 204, 222, 224, 226, 230.

In yet another embodiment, a variable frequency (i.e., stimulating a non-constant frequency) can be used at one or more of the electrodes 204, 222, 224, 226, 230. The variable frequency can be a sweep, and/or a random/pseudo-random frequency variability around a central frequency (e.g., 5 Hz+/−1.5 Hz, or 100 Hz+/−10 Hz).

In one embodiment, the auricular component 201, 600 is made with a single flexible board containing electronic components to uniquely identify it and, among other things, to counteract any inductance produced by the connecting cable. This flexible electronic circuit is over-molded onto a skin 502 allowing openings in it to allow direct contact with the back part of the skin-contacting electrodes 503. This auricular component 201, 600 is light-weight and extremely flexible allowing it to easily conform to different shapes presented by the anatomic variability of users. In one embodiment, the molded auricular component is not homogenic, changing the density and elasticity/flexibility at different places such that, for example, the part going around the ear is more flexible than the part going on the ear.

In other embodiment, the flexible electronic circuit 600 is covered with a flexible material such as a closed cell foam.

In one embodiment, the skin-contacting electrodes can be made for example of 3-layers, being the first layer a medical-grade double-sided conducting adhesive tape, the second layer a conductive flexible metallic and/or fabric mesh for mechanical robustness and homogenic electrical field distribution, and a third layer of self-adhesive hydrogel. A two-layer version is also possible in which both mechanical robustness and homogenic electrical field distribution is achieved by the first layer, rendering unnecessary the second layer described in the three-layer electrode.

In another embodiment, the PCB electrodes 503 are made such that they cover a similar surface area as the skin-contacting hydrogel electrodes; such that homogenic electrical field distribution is achieved at the hydrogels without the need of any additional conductive layer.

In an aspect, the system can record overall therapeutic delivery so the caregiver/clinician can measure compliance. In one embodiment, the management software notifies the wearer, caregiver, clinician if the device has stopped delivering therapy. In an example, the management software can be configured to report data related to use, events, logs, errors, and device health status. In an aspect, the system can provide usage reports. In an aspect, the system can have a uniquely identifiable auricular component 201 that can be used in identifying users and reported data. In an example, the device health status can report on the condition of the electrodes, the conductive hydrogel, and/or the analgesic.

In an exemplary embodiment, the system can utilize feedback to monitor and/or modify the therapy. In some implementations, the feedback can include one of electrodermal activity, movement activity, glucose monitoring, neuro-monitoring, EKG, EEG, blood pressure (systolic, diastolic and mean) imaging and any other type of sensing related to the symptoms and therapy. In an example, the electrodermal activity could be used to monitor and detect a speed or timing of a symptom and/or therapeutic outcome. In an example, the electrodermal activity could be sensed by electrodes on the auricular component 201. In another example, the electrodermal activity could be detected by electrodes on another portion of the body and communicated to the system.

In some implementations, the system can further include one or more accelerometers/gyroscopes that can be used gather information to modulate the therapy. In an example, the one or more accelerometers/gyroscopes is configured to detect a tremor and/or physiologic movement. In an aspect, the tremor and/or the physiologic movement can be indicative of at least one of the underlying condition and the treatment to the underlying condition. In an example, the tremor and/or physiologic movement can be indicative of symptoms associated with substance withdrawal. In an aspect, feedback from glucose monitoring can be used to modulate the therapy.

In yet other implementation, EKG can be used to assess heart rate and heart rate variability, to determine the activity of the autonomic nervous system in general and/or the relative activity of the sympathetic and parasympathetic branches of the autonomic nervous system, and to modulate the therapy. Autonomic nervous activity can be indicative of symptoms associated with substance withdrawal. In an aspect, the treatment device can be used to provide therapy for treating cardiac conditions such as atrial fibrillation and heart failure. In an example, therapy can be provided for modulation of the autonomic nervous system. In some implementations, the treatment device can be used to provide therapy to balance a ratio between any combinations of the autonomic nervous system, the parasympathetic nervous system, and the sympathetic nervous system.

In an aspect, the system can monitor impedance measurements allowing closed-loop neurostimulation. In an example, monitoring feedback can be used to alert patient/caregiver if therapy is not being adequately delivered and if the treatment device is removed.

Figure 15:
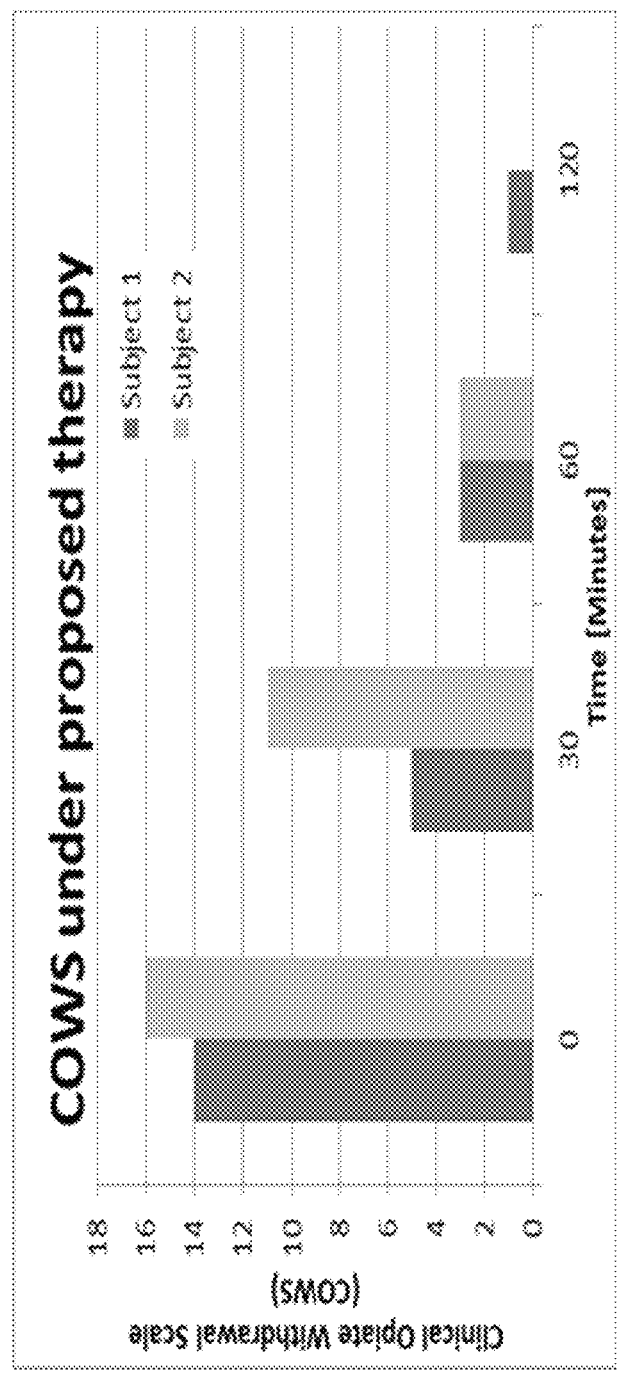
FIG. 15 is a bar graph showing data collected using the proposed system according to an example.

Turning to FIG. 15, a graph is shown of data collected using the proposed system according to an example. Clinical Opiate Withdrawal Score (COWS) over time was collected from subjects being treated with the proposed therapy. Therapy included using Low frequency (5 Hz) between the cymba electrode 204 and an electrode 224, and High frequency (100 Hz) between the auriculotemporal electrode 222 and electrode 226.

The invention claimed is:

1. A wearable treatment system for providing transcutaneous stimulation for inducing endogenous release of peptides, the treatment system comprising:
 a concha apparatus for placement external to an ear canal of an ear of a patient, including a first electrode configured to be in contact with vagal related neural structures of the ear of the patient, wherein
  the concha apparatus is configured to be retained, at least in part, through frictional engagement with a concha of the ear;
 a first connector;
 an earpiece for placement around the ear of the patient, the earpiece being connected to the concha apparatus by the first connector, the earpiece including
  an insulated electronics layer including
   a second electrode configured to be in contact with a neural structure related to the auriculotemporal nerve, and
   at least another electrode configured to be in contact with neural structures related to at least one of the great auricular nerve and/or branches of the great auricular nerve and/or the lesser occipital nerve and/or branches of the lesser occipital nerve;
 a second connector; and
 a pulse generator configured to be connected to the earpiece by the second connector, the pulse generator including circuitry in electrical communication with the first electrode of the concha apparatus via the first connector, and the second electrode and the at least another electrode of the earpiece via the second connector, wherein
  the circuitry is configured to provide a therapy that induces the endogenous release of peptides through pulses of electrical stimulation to the ear and/or around the ear of the patient via the first electrode, the second electrode, and the at least another electrode;
 wherein the concha apparatus and the earpiece are designed for secure placement of the first electrode, the second electrode, and the at least another electrode without piercing the dermal layers of skin on and surrounding the ear.

2. The treatment system of claim 1, further comprising a peripheral device configured to be in communication with the pulse generator and configured to modify a stimulation parameter of the therapy provided by the pulse generator to at least one electrode of the first electrode, the second electrode, and the at least another electrode.

3. The treatment system of claim 2, wherein the stimulation parameter is configured to cause the circuitry to synchronize at least a portion of the pulses of electrical stimulation delivered to the first electrode of the concha apparatus and the second electrode of the earpiece to balance a ratio of activity between at least one of a) the autonomic nervous system and the parasympathetic nervous system, b) the autonomic nervous system and the sympathetic nervous system, or c) the parasympathetic nervous system and the sympathetic nervous system.

4. The treatment system of claim 1, wherein the pulse generator includes a low power field-programmable gate array for controlling delivery of the therapy.

5. The treatment system of claim 1, wherein at least one of the second electrode and the at least another electrode is comprised of a grouping of two or more electrodes.

6. The treatment system of claim 1, further comprising a multiplexor in communication with two or more electrodes of the second electrode and/or the at least another electrode and configured to direct the pulses of electrical stimulation towards at least one of the two or more electrodes.

7. The treatment system of claim 1, further comprising at least one actuator disposed between the second electrode and a given electrode of the at least another electrode.

8. The treatment system of claim 1, wherein the concha apparatus comprises:
 a first member configured to fit within first natural extrusions and notches of the ear to aid in retaining the concha apparatus in the concha of the ear; and
 a second member configured to fit within second natural extrusions and notches of the ear to aid in retaining the concha apparatus in the concha of the ear.

9. The treatment system of claim 1, wherein the concha apparatus includes a spring configured to stress a structure of the concha apparatus to facilitate placement of the first electrode.

10. The treatment system of claim 1, wherein a structure of the concha apparatus is configured to be mechanically stressed to facilitate secure placement of the first electrode against the skin.

11. The treatment system of claim 1, wherein the pulses of electrical stimulation are configured to provide the endogenous release of peptides for treating substance use disorder and/or pain.

12. The treatment system of claim 1, wherein the pulses of electrical stimulation are configured to provide therapy for treatment of neonatal abstinence syndrome.

13. The treatment system of claim 1, wherein the pulses of electrical stimulation are configured to induce neuronal plasticity for at least one of provoking cognitive improvements, stroke recovery, PTSD, phobias, ADHD, ADD, dementia including treating Alzheimer's disease.

14. The treatment system of claim 1, wherein the pulses of electrical stimulation are configured to be used to restore autonomic balance to support treatment of at least one of cardiac heart failure, atrial fibrillation, anxiety, stress, gastric motility, depression, cluster headaches, and migraines.

15. The treatment system of claim 1, wherein the pulses of electrical stimulation are configured to provide therapy for treatment of inflammation.

16. The treatment system of claim 1, wherein the therapy induces the endogenous release of endorphins.

17. The treatment system of claim 1, wherein the pulses of electrical stimulation are configured to provide therapy for treatment of chronic pain.

18. The treatment system of claim 1, wherein the earpiece further comprises an adhesive configured to secure the second electrode and the at least another electrode to a portion of the skin surrounding the ear of the patient.

19. A wearable treatment device for providing transcutaneous stimulation for inducing endogenous release of peptides, the treatment device comprising:
a concha apparatus for placement external to an ear canal of an ear of a patient, including a first electrode configured to be in contact with vagal related neural structures of the ear of the patient, wherein
the concha apparatus is configured to be retained, at least in part, through frictional engagement with a concha of the ear;
a first connector; and
an earpiece for placement around the ear of the patient, the earpiece being connected to the concha apparatus by the first connector, the earpiece including
an insulated electronics layer including
a second electrode configured to be in contact with a neural structure related to the auriculotemporal nerve, and
at least another electrode configured to be in contact with neural structures related to at least one of the great auricular nerve and/or branches of the great auricular nerve and/or the lesser occipital nerve and/or branches of the lesser occipital nerve, and
an adhesive configured to secure the second electrode and the at
least another electrode to a portion of the skin surrounding the ear of the patient; and
a second connector;
wherein the wearable treatment device is configured to be connected to a pulse generator, the pulse generator including circuitry configured to be in electrical communication with the first electrode of the concha apparatus via the first connector, and the second electrode and the at least another electrode of the earpiece via the second connector for providing the transcutaneous stimulation for inducing the endogenous release of peptides;
wherein the wearable treatment device is designed for secure placement of the first electrode, the second electrode, and the at least another electrode without piercing the dermal layers of skin on and surrounding the ear.

20. The treatment system of claim 18, wherein the adhesive comprises a conductive adhesive coating on each electrode of the second electrode and the at least another electrode.

* * * * *

UNITED STATES PATENT AND TRADEMARK OFFICE
CERTIFICATE OF CORRECTION

| | |
|---|---|
| PATENT NO. | : 10,695,568 B1 |
| APPLICATION NO. | : 16/510930 |
| DATED | : June 30, 2020 |
| INVENTOR(S) | : Alejandro Covalin |

It is certified that error appears in the above-identified patent and that said Letters Patent is hereby corrected as shown below:

In the Specification

Column 2, Line 61:
Delete:
"imbalance"
And insert:
-- balance --.

Column 11, Line 17:
Delete:
"imbalance"
And insert:
-- balance --.

Signed and Sealed this
Twenty-fifth Day of April, 2023

Katherine Kelly Vidal
*Director of the United States Patent and Trademark Office*